(12) United States Patent
Yoon et al.

(10) Patent No.: US 8,618,298 B2
(45) Date of Patent: Dec. 31, 2013

(54) PERYLENE TETRACARBOXIMIDE DERIVATIVES FOR PHOTOVOLTAIC DEVICES

(75) Inventors: Ung Chan Yoon, Busan (KR); Myung Ho Hyun, Busan (KR); Hong-Seok Kim, Daegu (KR); Sang-Jin Moon, Daejeon (KR); Won Suk Shin, Daejeon (KR); Young In Kim, Busan (KR); Ok-Sang Jung, Busan (KR)

(73) Assignee: Solvay SA, Brussels (BE)

( * ) Notice: Subject to any disclaimer, the term of this patent is extended or adjusted under 35 U.S.C. 154(b) by 203 days.

(21) Appl. No.: 13/055,939

(22) PCT Filed: Jul. 28, 2009

(86) PCT No.: PCT/EP2009/059711
§ 371 (c)(1),
(2), (4) Date: Jan. 26, 2011

(87) PCT Pub. No.: WO2010/012710
PCT Pub. Date: Feb. 4, 2010

(65) Prior Publication Data
US 2011/0130566 A1    Jun. 2, 2011

(30) Foreign Application Priority Data
Jul. 29, 2008  (EP) .................................. 08161385

(51) Int. Cl.
*C07D 471/08* (2006.01)
*H01L 51/00* (2006.01)

(52) U.S. Cl.
USPC .............................. 546/37; 313/498; 313/504

(58) Field of Classification Search
USPC ....................................... 546/37; 313/504, 498
See application file for complete search history.

(56) References Cited

FOREIGN PATENT DOCUMENTS

| DE | 102005045375 A1 | 3/2007 |
|---|---|---|
| DE | 102006048638 A1 | 4/2008 |
| JP | 02196885 A | 8/1990 |
| JP | 10006645 A | 1/1998 |
| WO | WO 2007/042474 A2 | 4/2007 |
| WO | WO 2008/012584 A1 | 1/2008 |

OTHER PUBLICATIONS

Cremer et. al.—"Perylene-Oligothiophene-Perylene Triads for Photovoltaic Applications", Eur. J. Org. Chem. 2005, pp. 3715-3723, published by Wiley-VCH Verlag GmbH & Co. (9 pg.).
Chen et. al.—"Oligothiophene-Functionalized Perylene Bisimide System: Synthesis, Characterization, and Electrochemical Polymerization Properties", Chem. Mater. 2005, vol. 17, pp. 2208-2215, published by American Chemical Society (8 pg.).
Xiaowei et. al.—"A High-Mobility Electron-Transport Polymer with Broad Absorption and Its Use in Field-Effect Transistors and All-Polymer Solar Cells", Journal of American Chemical Society Communications, 2007, vol. 129, pp. 7246-7247 (2 pg.).
Huang et. al.—"Size Effects of Oligothiophene on the Dynamics of Electron Transfer in π-Conjugated Oligothiophene-Perylene Bisimide Dyads", J. Phys. Chem. C 2008, vol. 112, pp. 2689-2696, published by American Chemical Society ( 8 pg.).
Reynolds et. al.—"Spectral Broadening in MEH-PPV:PCBM-Based Photovoltaic Devices via Blending with a Narrow Band Gap Cyanovinylene-Dioxythiophene Polymer", Macromolecules, 2005, vol. 38 (13), pp. 5359-5362, published by American Chemical Society (4 pg.).
Blouin et. al.—"Toward a Rational Design of Poly(2,7-Carbazole) Derivatives for Solar Cells", Journal of American Chemical Society Articles, 2008, 130 (2), pp. 732-742, published by American Chemical Society (11 pg.).
Scharber. et. al.—"Design Rules for Donors in Bulk-Heterojunction Solar Cells—Towards 10 % Energy-Conversion Efficiency", Advanced Materials, vol. 18, Issue 6, Mar. 2006, pp. 789-794, published by Wiley-VCH Verlag GmbH & Co. (6 pg.).

(Continued)

*Primary Examiner* — Charanjit Aulakh
(74) *Attorney, Agent, or Firm* — Foley & Lardner LLP

(57) ABSTRACT

The compounds of the present invention are represented by the following formula (I):

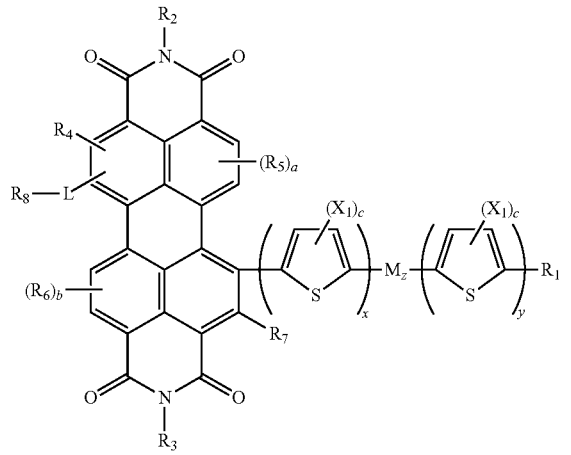

wherein M is represented by the following formula:

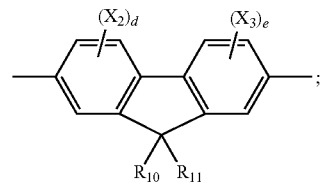

with $R_1$, $R_2$, $R_3$, $R_4$, $R_5$, $R_6$, $R_7$, $R_8$, $R_{10}$, $R_{11}$, $X_1$, $X_2$, $X_3$, L, a, b, c, d, e, x, y, and z defined herein.

12 Claims, 7 Drawing Sheets

(56) References Cited

OTHER PUBLICATIONS

Iden et. al.—"Fluorescent dyes for solar collectors", Forschungsber-Bundesminist. Forsch. Technol., Technol. Forsch. Entwickl. (1984), BMFT-FB-T 84-164, 115 pp.—attached CAS abstract in English only (1 pg.).
Alvino et. al.—"Synthesis and spectroscopic properties of highly water-soluble perylene derivatives", Tetrahedron, Aug. 13, 2007, vol. 63, Issue 33, pp. 7858-7865, published by Elsevier Ltd ( 8 pg.).
U.S. Appl. No. 12/089,303, filed Aug. 18, 2008, Sung Jo Jin et al.

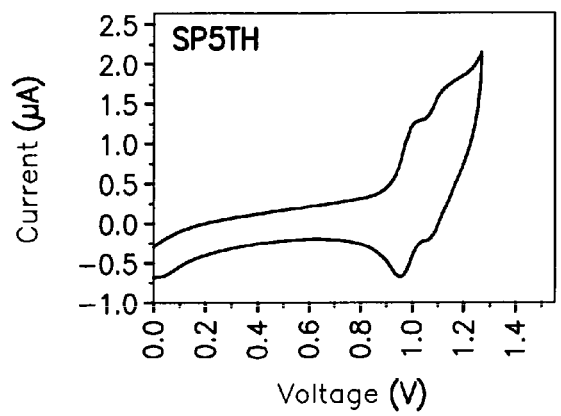
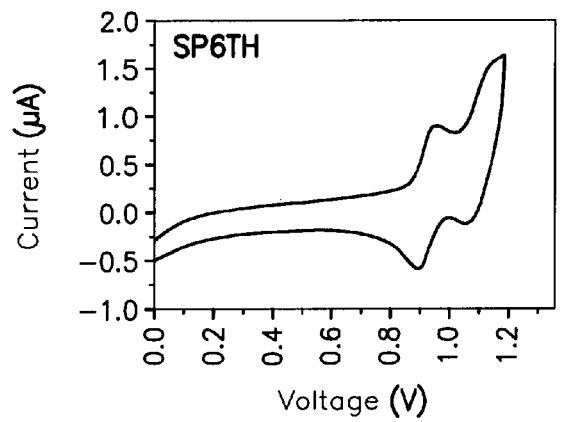
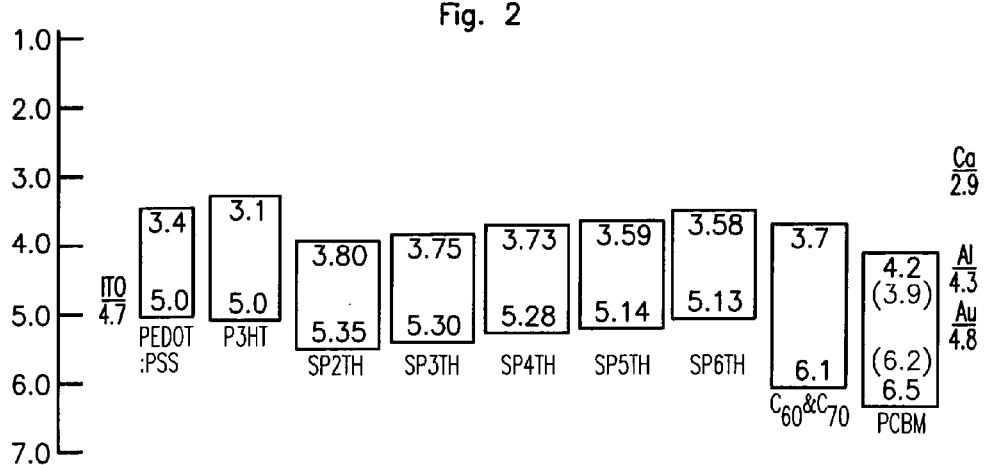

Triplet $\tau$ = 5.8μs (iridium complex)

Slope = $kq \cdot \tau$ = $6.2 \times 10^4$
SP2T; $kq$ = $1.1 \times 10^{10}$ $M^{-1}s^{-1}$
(Diffusion controlled)

PERYLENE TETRACARBOXIMIDE DERIVATIVES FOR PHOTOVOLTAIC DEVICES

CROSS-REFERENCE TO RELATED APPLICATIONS

This application is a U.S. national stage application under 35 U.S.C. §371 of International Application No. PCT/EP2009/059711 filed Jul. 28, 2009, which claims priority to European Application No. 08161385.3 filed Jul. 29, 2008, this application being herein incorporated by reference in its entirety for all purposes.

TECHNICAL FIELD

The present invention relates to perylene tetracarboximide derivatives. The present invention further relates to oligothiophene-conjugated perylene tetracarboximides (TCPTCDI) and the use thereof in photovoltaic devices.

BACKGROUND

Photovoltaic devices are used to convert light into electrical energy. Photovoltaic devices are characterized by their efficiency with which they can convert incidental light to useful electrical energy.

Traditionally, photovoltaic devices have been made of various inorganic semiconductors, e.g., crystalline, polycrystalline, and amorphous silicon, gallium arsenide, cadmium telluride, and others. Devices utilizing crystalline or amorphous silicon dominate commercial applications, and some have achieved high efficiencies. However, it is difficult and expensive to produce efficient crystalline-based devices, especially of large surface area, due to the inherent difficulties in producing large crystals without significant efficiency-degrading defects. Further, high efficiency amorphous silicon devices have problems with stability.

Recently, organic photovoltaic (OPV) devices are being researched and developed to achieve acceptable photovoltaic conversion efficiencies with economical production costs. However, since the energy conversion efficiencies of OPV devices are still low in comparison to their inorganic counterparts due to mainly very weak molecular orbital coupling and subsequent low carrier mobility of organic semiconductor, the industrial production of organic solar cells is not yet economical. One promising approach to circumvent the problem of low carrier mobility and small exciton diffusion bottleneck and thus to increase the overall energy conversion efficiencies of organic solar cells is the utilization of hetrojunction OPV or dispersed heterojunction OPV with a donor-acceptor system, consisting of n- and p-type conducting materials in a double layers separately (hetrojunction OPV) or a single layer prepared by blending the two n- and p-type materials (dispersed heterojunction OPV). The success and efficiency of dispersed hetrojunction OPV is largely depend on the domain size of interpenetrating donor-acceptor network whose size is ideally in the range of 10 nm. Since the degree of interpenetrating phase separation and the domain size depend on the choice of the solvent, speed of evaporation, solubility, miscibility of the donor and acceptor, etc., controlling the morphology of the organic compound in dispersed heterojunction devices is critical.

One way of controlling the morphology of an organic compound is to produce a molecular heterojunction by covalently linking electron-donor and acceptor molecules. Due to their unique optical and electrical properties, molecular heterojunction materials, i.e., donor-acceptor linked molecules, are likely to have important applications in OPV devices and, thus, have triggered intense scientific research.

Among the electron-donor and acceptor materials that are capable of producing a molecular heterojunction, oligothiophene and perylene tetracarboximide functional units have been extensively studied since the former preserves its typical charge-transport and self-assembling properties, while the latter provides high molar absorptivity in the visible region as well as electron-accepting properties. For example, Cremer et al., "Perylene-Oligothiophene-Perylene Triads for Photovoltaic Applications," *Eur. J. Org. Chem.*, 3715-3723 (2005) discloses acceptor-donor-acceptor triad systems consisting of head-to-tail-coupled oligo(3-hexylthiophenes) integrated between two terminal perylenemonoimides which can be used for organic solar cells. In addition, Chen et al., "Oligothiophene-Functionalized Perylene Bisimide System: Synthesis, Characterization, and Electrochemical Polymerization Properties," *Chem. Mater.*, 17:2208-2215 (2005) describes perylene bisimides derivatives functionalized with two oligothiophene substituents. Further, Xiaowei et al., "A High-Mobility Electron-Transport Polymer with Broad Absorption and Its Use in Field-Effect Transistors and All-Polymer Solar Cells," *J. Am. Chem. Soc.* 129:7246-7247 (2007) discloses a copolymer of perylene diimide and dithienothiophene building blocks exhibiting broad absorption ranging from the visible to the near infrared regions. Huang et al., "Size Effects of Oligothiphene on the Dynamics of Electron Transfer in π-Conjugated Oligothiophene-Perylene Bisimide Dyads," *J. Phys. Chem. C* 112:2689-2696 (2008) discloses the preparation of a series of π-conjugated perylene bisimide dyads having two oligothiophene moieties, while PCT International Publication No. WO 08012584A describes several perylene tetracarboximides as hole-transporting materials for light emitting devices.

However, none of the above compounds disclosed in the art exhibits sufficiently high efficiency, charge carrier mobility, or stability when utilized in OPV devices. It would thus be desirable to develop perylene tetracarboximide derivatives that have potentials for ideal electron donor for fullerene derivative [6,6]-phenyl-$C_{61}$-butyric acid methyl ester (PCBM), high photovoltaic conversion efficiencies and are stable for OPV device applications.

BRIEF DESCRIPTION OF THE DRAWINGS

FIGS. 1*a-e* are cyclic voltammograms of the TCPTCDIs of the present invention.

FIGS. 2 and 3 are energy band diagrams of the TCPTCDIs of the present invention and other OPV materials.

DETAILED DESCRIPTION OF THE INVENTION

Figure 1A:
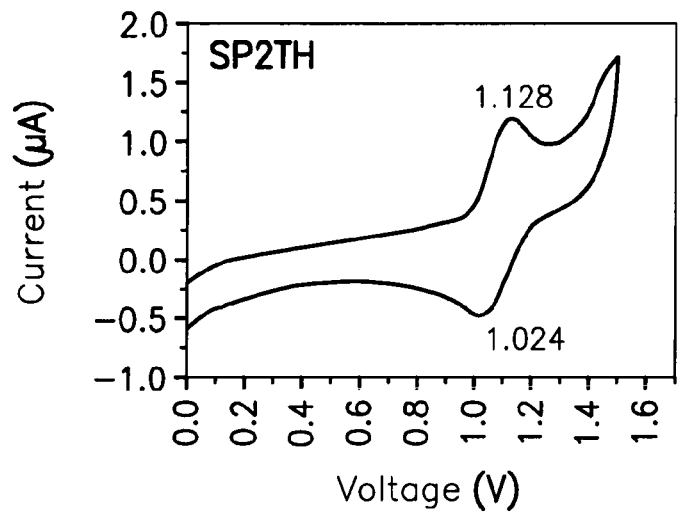
Figure 1B:
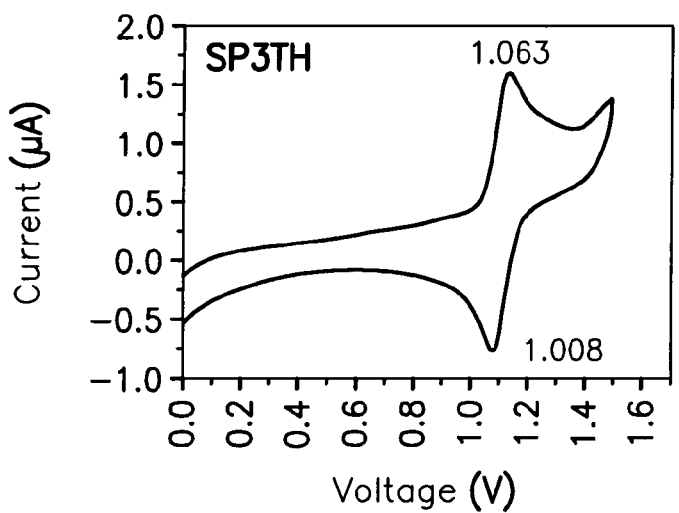
Figure 1C:
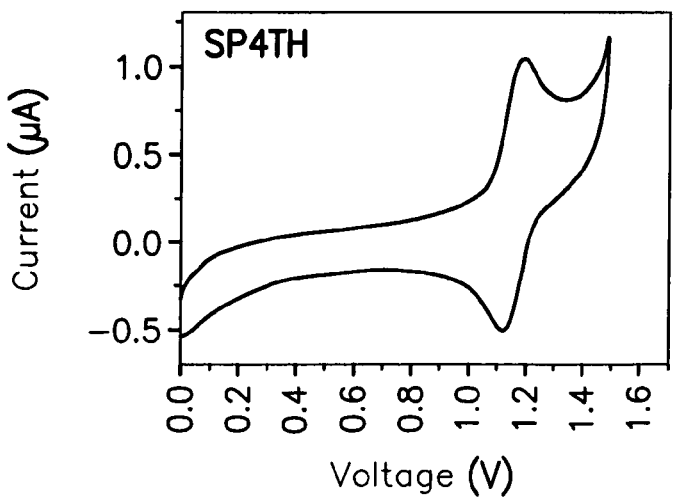

The present invention relates to oligothiophene-conjugated perylene tetracarboximide (TCPTCDI) derivatives and the use thereof, as well as molecular heterojunction materials comprising the same for OPV devices. The TCPTCDI derivatives of the present invention may act as electron donor, acceptor, or donor-acceptor linked molecules in OPV devices.

In one embodiment, the TCPTCDI derivatives of the present invention can be represented by formula (I):

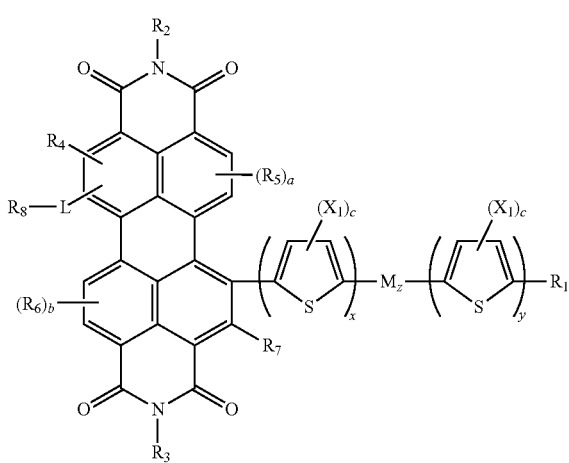

(I)

wherein:
M is represented by the following formula:

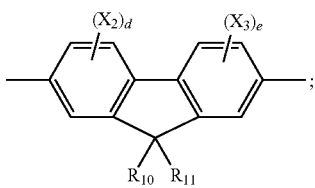

$R_1, R_2, R_3, R_4, R_5, R_6, R_7, R_8, R_{10}, R_{11}, X_1, X_2,$ and $X_3$ are the same or different at each occurrence and are selected from the group consisting of —H, —F, —Cl, —Br, —NO$_2$, —CN, a straight or branched $C_{1-20}$ alkyl, a $C_{2-20}$ alkene, a $C_{2-20}$ alkyne, a $C_{3-20}$ cyclic alkyl, a straight or branched $C_{1-20}$ alkoxy, a $C_{1-20}$ dialkylamino, a $C_{4-20}$ polyoxaalkyl, a $C_{4-20}$ polythioalkyl, a $C_{4-20}$ polyazaalkyl, a $C_{4-14}$ aryl, and a $C_{4-14}$ heteroaryl which may be substituted with one or more non-aromatic radicals, wherein $R_{10}$ and $R_{11}$ or any of $R_1, R_2, R_3, R_4, R_5, R_6, R_7, R_8,$ and $X_1$ may in turn together form a mono- or polycyclic ring, optionally aromatic;

L is selected from the group consisting of —NR$_9$—, —PR$_9$—, —O—, and —S—, wherein R$_9$ is selected from the group consisting of —H, —F, —Cl, —Br, —NO$_2$, —CN, a straight or branched $C_{1-20}$ alkyl, a $C_{2-20}$ alkene, a $C_{2-20}$ alkyne, a $C_{3-20}$ cyclic alkyl, a straight or branched $C_{1-20}$ alkoxy, a $C_{1-20}$ dialkylamino, a $C_{4-20}$ polyoxaalkyl, a $C_{4-20}$ polythioalkyl, a $C_{4-20}$ polyazaalkyl, a $C_{4-14}$ aryl, and a $C_{4-14}$ heteroaryl which may be substituted with one or more non-aromatic radicals;

a, b, and c are the same or different at each occurrence and are an integer from 0 to 2;

d and e are the same or different at each occurrence and are an integer from 0 to 3;

x and y are the same or different at each occurrence and are an integer from 0 to 4; and z is 0 or 1.

The term "alkyl" as used herein refers to hydrocarbon radicals containing preferably 1 to 20, more preferably 1 to 10, most preferably 1 to 6 carbon atoms. Specific examples thereof include, but are not limited to, methyl, ethyl, propyl, isopropyl, butyl, t-butyl, pentyl, hexyl, and heptyl groups.

The term "alkene" as used herein refers to hydrocarbon radicals having at least one double bond, containing preferably 2 to 20, more preferably 2 to 10, most preferably 2 to 6 carbon atoms. The term "alkyne" as used herein refers to hydrocarbon radicals having at least one triple bond, containing preferably 2 to 20, more preferably 2 to 10, most preferably 2 to 6 carbon atoms.

The term "alkoxy" as used herein refers to an alkyl group containing preferably 1 to 20, more preferably 1 to 10, most preferably 1 to 6 carbon atoms, covalently bound to an oxygen atom. Specific examples thereof include, but are not limited to, methoxy, ethoxy, propyloxy, isopropyloxy, butoxy, t-butoxy, pentyloxy, hexyloxy, and heptyloxy groups.

The term "cyclic alkyl" as used herein refers to cyclic hydrocarbon radicals containing preferably 3 to 20, more preferably 3 to 10, most preferably 5 or 6 carbon atoms, which do not give steric hindrance. Specific examples thereof include, but are not limited to, cyclopentyl and cyclohexyl groups.

The term "aryl" as used herein refers to carbocyclic rings with a degree of unsaturation present so as to impart aromaticity to the ring. Specific examples thereof include, but are not limited to, phenyl, naphthyl, anthracenyl, biphenyl, pyrenyl, and perylene groups.

The term "heteroaryl" as used herein refers to a substituted or unsubstituted heterocyclic aromatic ring, which can be a five-member ring heterocycle, a six-member ring heterocycle, or a ring-fused bicyclic heterocycle. Specific examples thereof include, but are not limited to, pyridyl, bipyridyl, acridyl, thiophene, imidazole, oxazole, thiazole, and quinolinyl groups.

The term "polyoxa-, polythio-, and polyaza-" as used herein refers to hydrocarnon radicals containing more than two oxygen, sulphur, and nitrogen atoms in the chain.

The perylene tetracarboximides of particular interest in the frame of the invention preferably have at least x or y which is not equal to zero and even more particularly, x+y which is equalt to or higher than 2. Hence, of particular interest are perylene tetracarboximides having π-conjugated oligothiophene groups. As the number of thiophene repeating unit increases, the electronic interactions between the perylene tetracarboximides and the thiophene units also increase. By changing the number of the thiophene repeating units, it is possible to control the energy levels of high occupied molecular orbital (HOMO) and low unoccupied molecular orbital (LUMO) of the compounds.

In one embodiment of the present invention, $R_1$ is —H or a straight or branched $C_{1-20}$ alkyl which may be substituted with one or more non-aromatic radicals. Preferably, $R_1$ is —H or a $C_{1-6}$ alkyl.

In another embodiment of the present invention, $R_1$ is selected from a cyano or carboxyl group. Introducing electron-withdrawing cyano groups at the end of the oligothiophene units, while adding an extra olefin-conjugated moiety, might lower the energy levels (i.e., HOMO/LUMO) and allow smaller energy gap of the compound, leading to a better electron accepting ability. Further, the electron-withdrawing carboxyl group at the end might also make the compound useful as a light absorbing dye for dye-sensitized solar cells (DSSCs). For example, $R_1$ may be selected from the group consisting of,

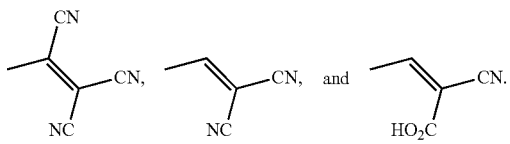

has been found that the solubility and self-assembling property of the compound can be improved by selecting an appropriate $R_8$. In one embodiment of the present invention, $R_8$ is a straight or branched $C_{1-20}$ alkyl which may be substituted with one or more substituent represented by the following formula:

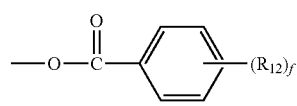

wherein $R_{12}$ is selected from the group consisting of —F, —Cl, —Br, —NO$_2$, —CN, a straight or branched $C_{1-20}$ alkyl, a $C_{2-20}$ alkene, a $C_{2-20}$ alkyne, a $C_{3-20}$ cyclic alkyl, a straight or branched $C_{1-20}$ alkoxy, a $C_{1-20}$ dialkylamino, a $C_{4-20}$ polyoxaalkyl, a $C_{4-20}$ polythioalkyl, a $C_{4-20}$ polyazaalkyl, a $C_{4-14}$ aryl, and a $C_{4-14}$ heteroaryl which may be substituted with one or more non-aromatic radicals, wherein, when f is an integer of at least 2, a plurality of $R_{12}$ may in turn together form a mono- or polycyclic ring, optionally aromatic; and f is an integer from 0 to 5.

Specific compounds of the present invention include compounds represented by the following Formula II:

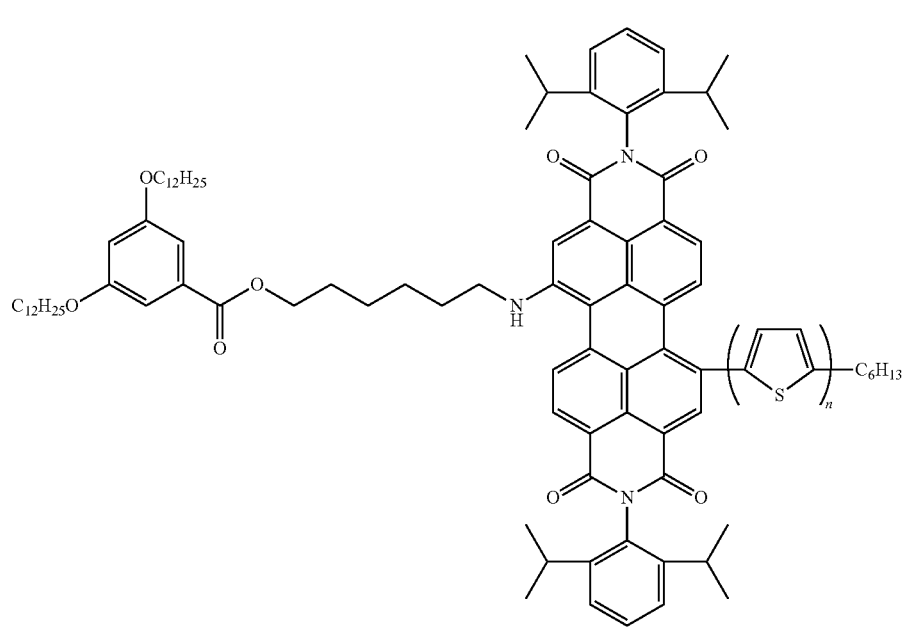

wherein n is an integer from 2 to 6.

The compounds of Formula II, where n is 2, 3, 4, 5, and 6, are designated as SP2TH, SP3TH, SP4TH, SP5TH, and SP6TH, respectively.

Other specific compounds of the present invention include compounds represented by the following Formula III:

Preferably, $R_2$ and $R_3$ are $C_{4-14}$ aryl which may be substituted with one or more non-aromatic radicals. More preferably, both $R_2$ and $R_3$ are a 2,6-diisopropylphenyl group.

Preferably, all of $R_4$, $R_5$, $R_6$, and $R_7$ are —H.

By introducing a soluble and self-assembling part into the compound, the photovoltaic performance was enhanced. It

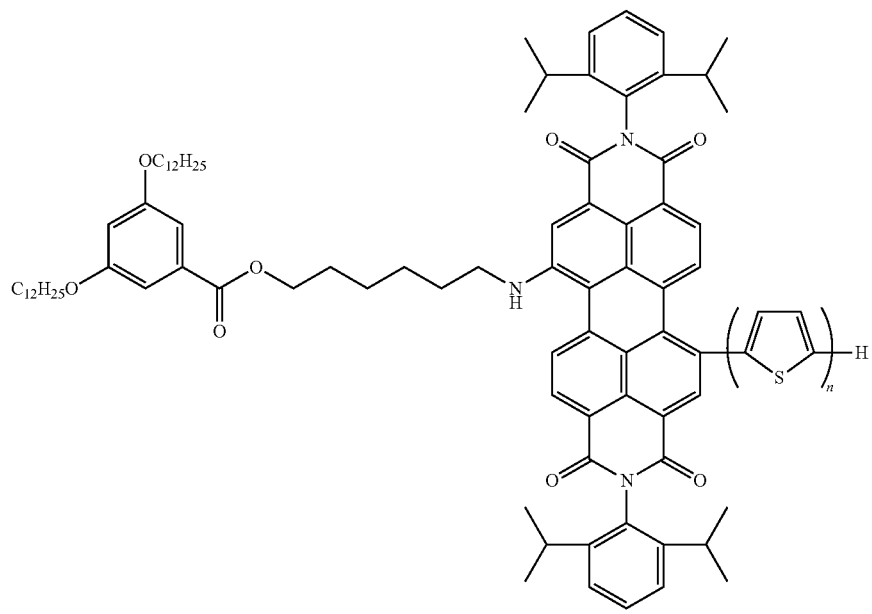

(III)

wherein n is an integer from 2 to 6.

The compounds of Formula III, where n is 2, 3, 4, 5, and 6, are designated as SP2T, SP3T, SP4T, SP5T, and SP6T, respectively.

The following examples are provided to illustrate embodiments of the present invention but are by no means intended to limit its scope.

EXAMPLES

The following scheme shows a synthetic pathway for a PTCDI derivative of the present invention.

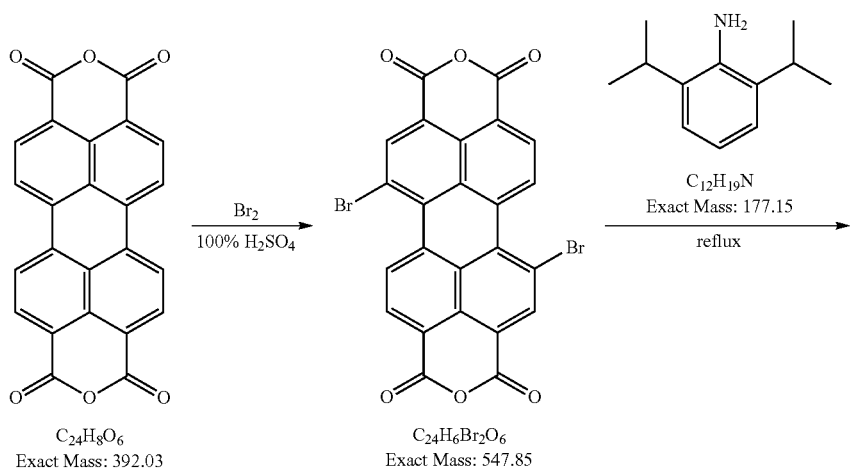

-continued
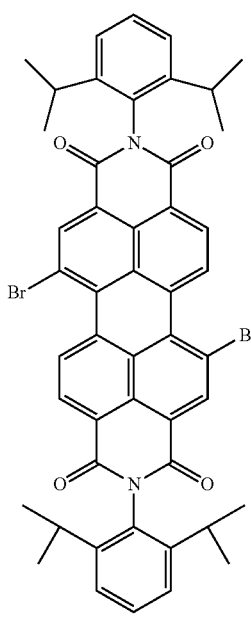
C₄₈H₄₀Br₂N₂O₄
Exact Mass: 866.14
6-aminohexanol
CHCl₃•rt
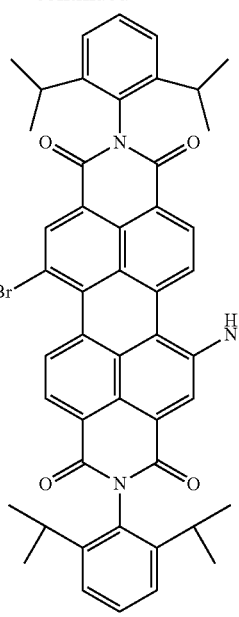
C₄₉H₄₃BrN₂O₅
Exact Mass: 818.24
3,5-bis(dodecycloxy)benzoic acid
DCC, DMAP, CH₂Cl₂, rt
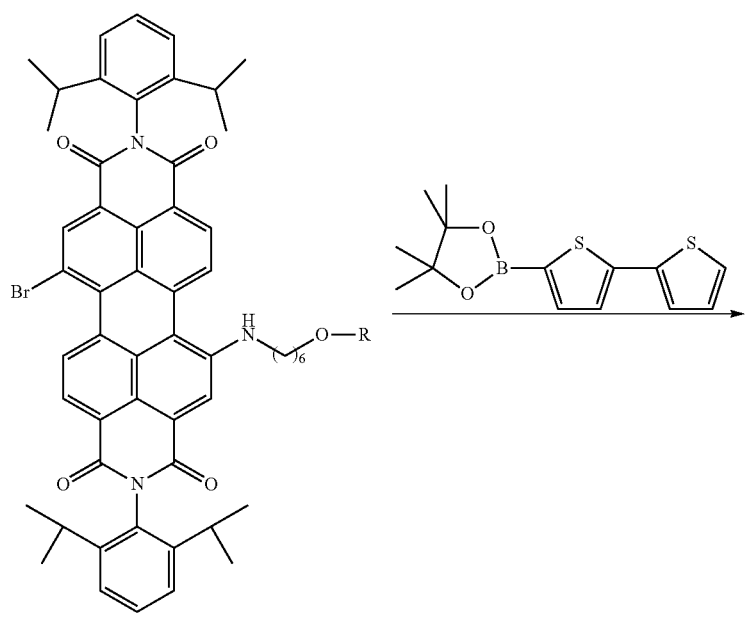

11 -continued 12
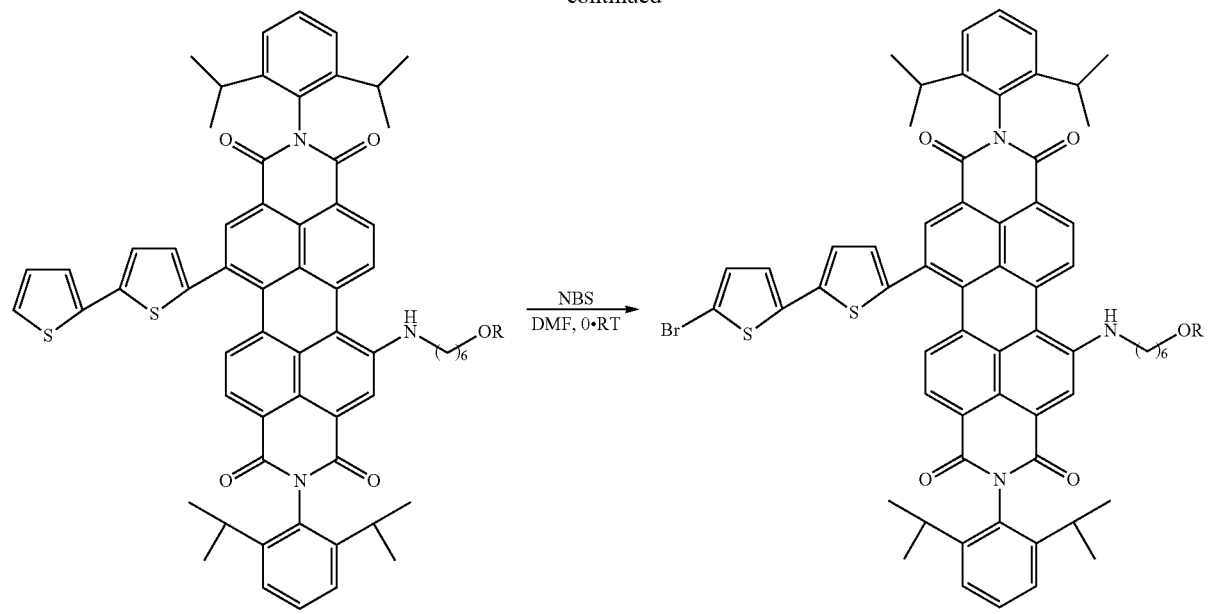
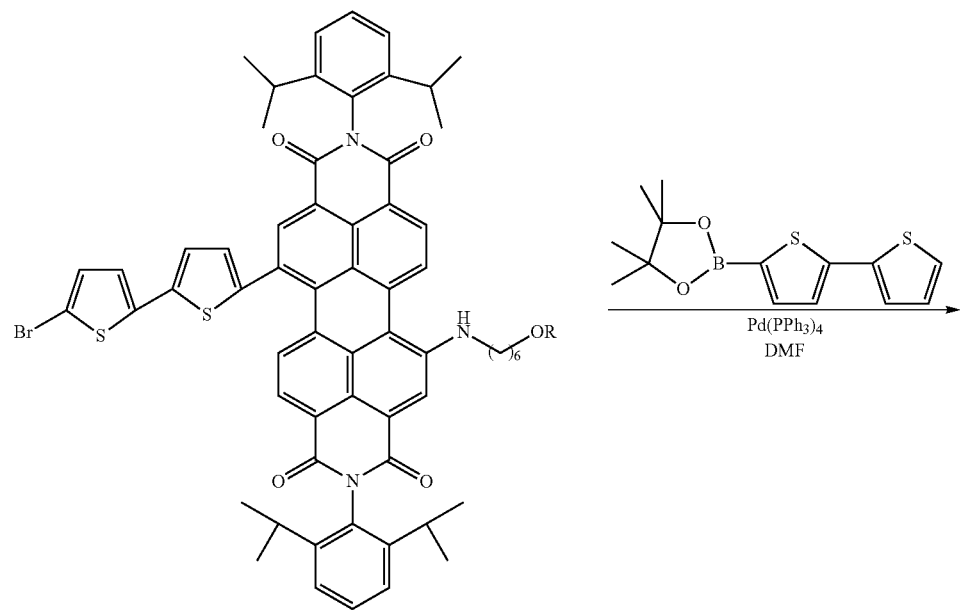

-continued
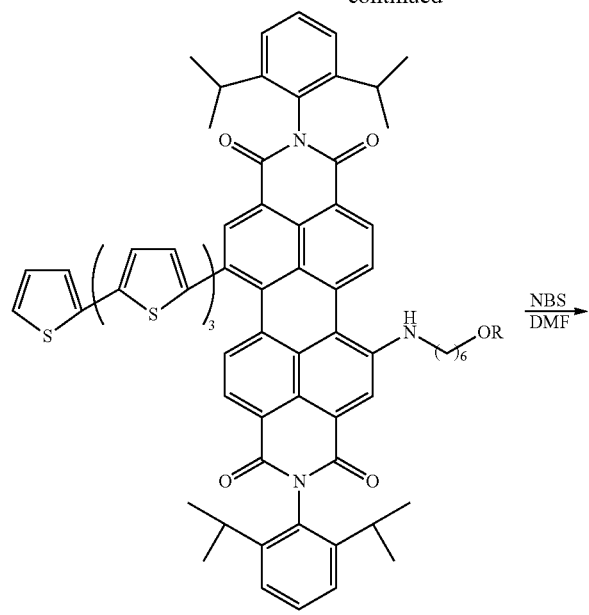
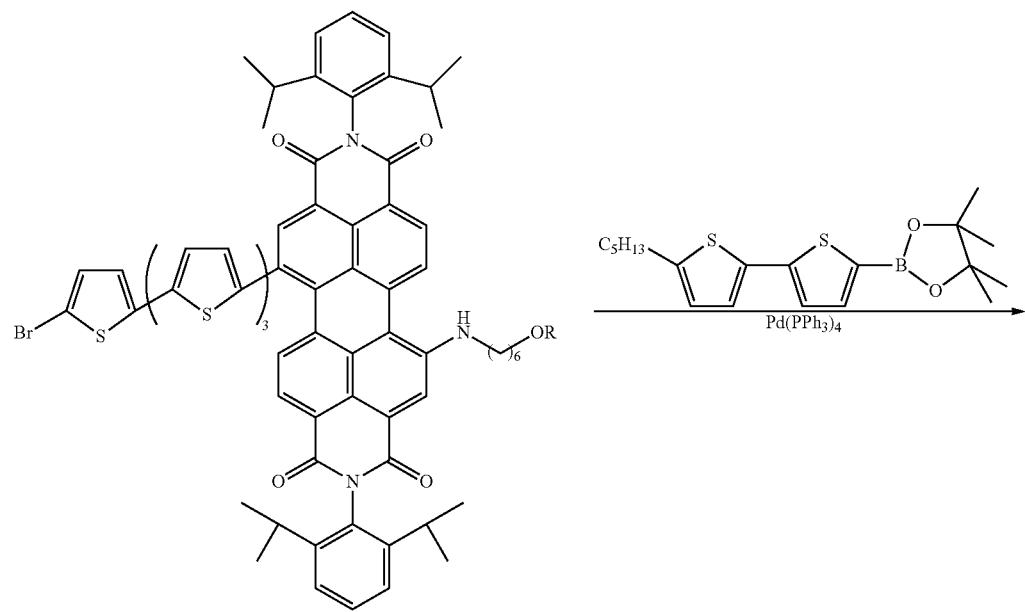

-continued

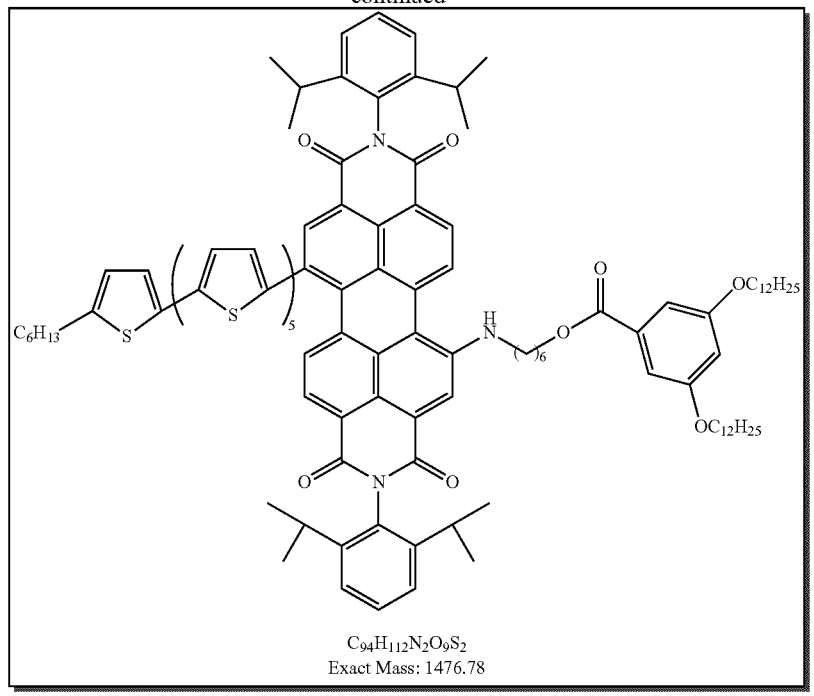

C$_{94}$H$_{112}$N$_2$O$_9$S$_2$
Exact Mass: 1476.78

All reagents were obtained from commercial sources and purified and dried according to standard procedures. Perylene-3,4,9,10-tetra-carboxylic dianhydride, 2,6-diisopropylaniline, 2-bromothiophene, 1-bromododecane, Pd(PPh$_3$)$_4$, 1-amino-6-hexanol, 3,5-dihydroxybenzoic acid, N-bromosuccinimide (NBS), dimethylaminopyridine (DMAP), dicyclohexylcarbodiimide (DCC), 2-isopropoxy-4,4,5,5-tetramethyl-1,3,2-dioxaborolane were purchased from Aldrich. Perylene tetracarboximides (PTCDI), bithiophene and their derivatives and 3,5-bis(dodecyloxy) benzoic acid were synthesized according to reported procedures.

Example 1

Synthesis of 1,7-dibromoperylene-3,4,9,10-tetracarboxylic dianhydride

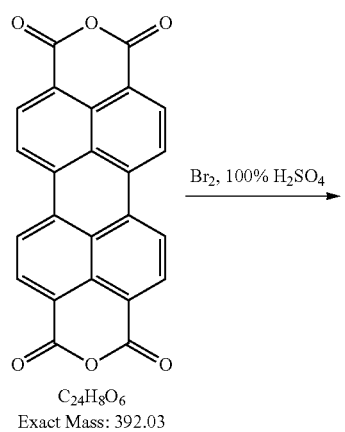

C$_{24}$H$_8$O$_6$
Exact Mass: 392.03

Br$_2$, 100% H$_2$SO$_4$

-continued

C$_{24}$H$_6$Br$_2$O$_6$
Exact Mass: 547.85

Perylene-3,4,9,10-tetra-carboxylic dianhydride (32 g, 81.4 mmol) was dissolved in 450 mL of 98% H$_2$SO$_4$ and then 0.77 g (3.03 mmol) of iodine was added in the reaction mixture and stirred at room temperature (RT) for 2 h. The reaction temperature was set at 80° C. and then 9.2 mL (180 mmol) of bromine was added dropwise over 2 h. The reaction was conducted at the same temperature for 16 h. The reaction mixture was cooled to RT, and the excess Br$_2$ was displaced by purging with N$_2$. The product was precipitated by an addition of ice water and collected by suction filtration. The precipitate was washed with water several times until the aqueous layer became neutral to yield dibromo-dianhydride as a crude product. The crude product was dried under reduced pressure at 120° C.

Example 2

Synthesis of N,N'-bis(2,6-diisopropylphenyl)-1,7-dibromoperylene-3,4,9,10-tetracarboxydiimide

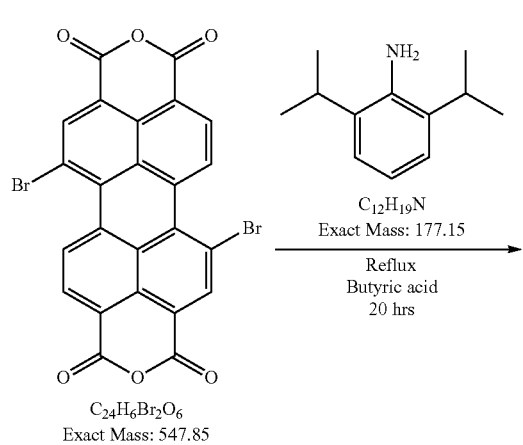

The crude dibromo compound (2.75 g, 5 mmol) was dissolved in 5 mL of acetic acid and 20 mL of N-methylpyrrolidone (NMP) was added. 2.21 g (12.5 mmol) of 2,6-diisopropylaniline was added into the reaction mixture and then the reaction mixture was refluxed for 120 h. The mixture was cooled down to RT and then poured onto crushed ice. The solid was filtered and washed with water and then dried in the oven for one day. The residue was purified by a column (silica gel, 5% ethyl acetate in n-hexane) to provide the product, diamino-diimide (37%) as an orange colored solid. $^1$H-NMR (300 MHz, CDCl$_3$) δ 9.58 (d, 2H), 9.02 (s, 2H), 8.81 (d, 2H), 7.51 (t, 2H), 7.34 (d, 4H), 2.7-2.8 (septet, 4H), 1.11 (d, 24H).

Example 3

Synthesis of N,N'-bis(2,6-diisopropylphenyl)-1-bromo-7-(6-hydroxy hexylamino)perylene-3,4,9,10-tetracarboxydiimide

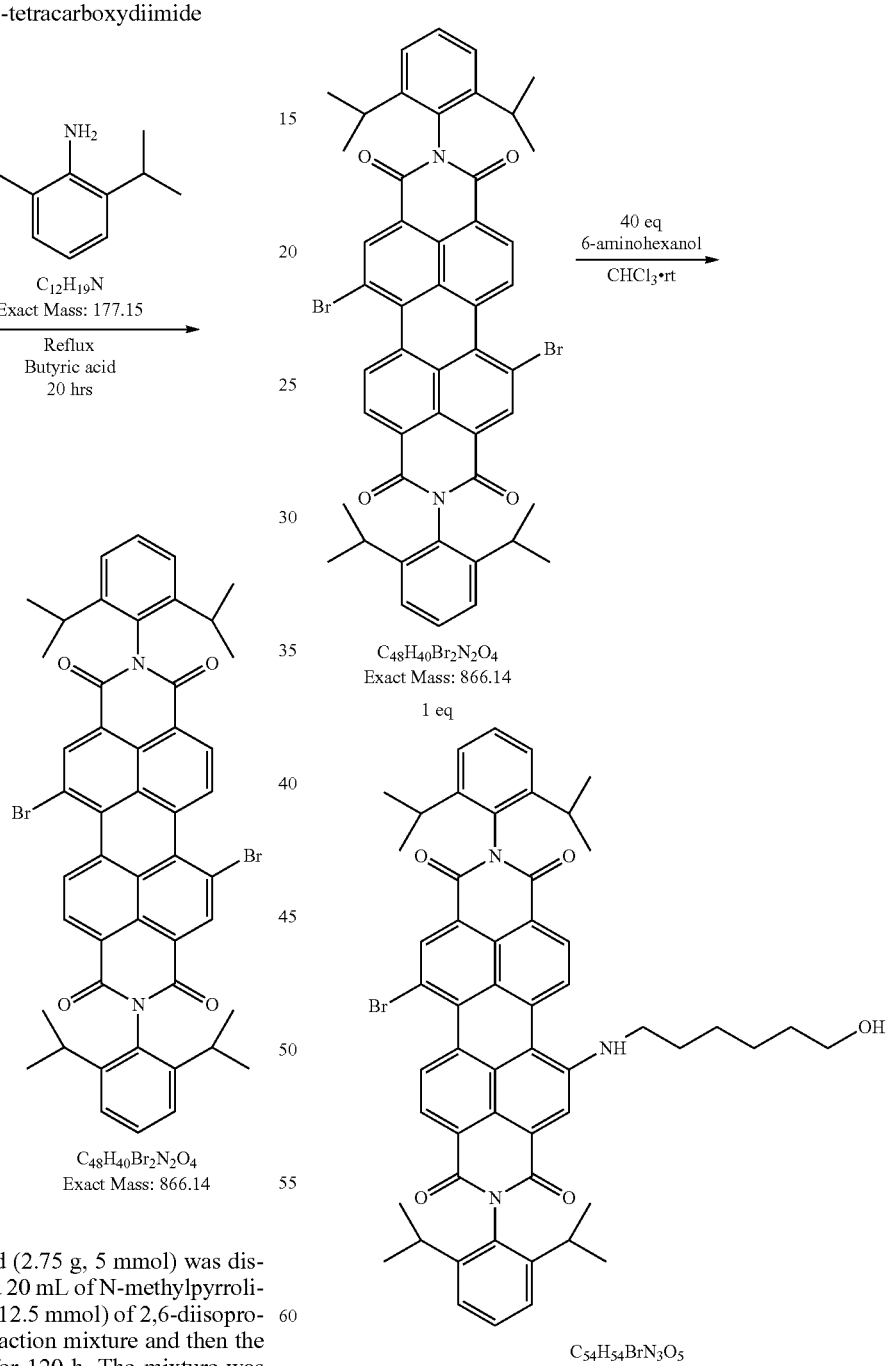

To a solution of diamino-diimide (0.433 g, 0.5 mmol) in 25 mL of CHCl$_3$ under nitrogen atmosphere, 2.4 g (20 mmol) of 1-amino-6-hexanol was added at RT. The resulting orange solution was stirred at a 70° C. temperature under nitrogen for 72 h. The reaction mixture was poured into 2N—HCl. The organic phase was extracted with methylene chloride (MC), washed with water and 2N—HCl solution and then the organic extract was stored over MgSO$_4$. The solvent was removed by rotary evaporation and the residue was purified by a column (silica gel, 40% ethyl acetate and n-hexane) to provide 36% of the product as a green solid. $^1$H-NMR (300 MHz, CDCl$_3$) δ 9.48 (d, 1H), 9.02 (s, 1H), 8.81 (d, 1H), 8.70 (d, 1 H), 8.51 (d, 1H), 8.31 (s, 1H), 7.51 (t, 2H), 7.34 (d, 4H), 6.2 (t, NH), 3.63-3.7 (m, 2H), 3.5-3.6 (m, 2H), 2.6-2.8 (septet, 4H), 1.8-1.88 (q, 2H), 1.51-1.67 (m, 6H), 1.11 (d, 24H).

Example 4

Synthesis of methyl 3,5-dihydroxybenzoate

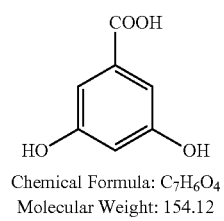

Chemical Formula: C$_7$H$_6$O$_4$
Molecular Weight: 154.12

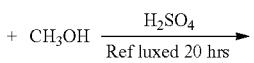

+ CH$_3$OH  $\xrightarrow{\text{H}_2\text{SO}_4}{\text{Refluxed 20 hrs}}$

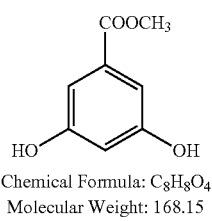

Chemical Formula: C$_8$H$_8$O$_4$
Molecular Weight: 168.15

A solution of 3,5-dihydroxybenzoic acid (20.0 g, 129.9 mmol) in dry methanol (100 mL) and H$_2$SO$_4$ (1 mL) was refluxed for 20 h. The volatile product was removed in vacuo and the residue was redissolved in ethyl acetate (EA) and washed with aqueous NaHCO$_3$, water and brine. The organic phase was dried with anhydrous sodium sulphate and the solvent was evaporated to yield methyl 3,5-dihydroxybenzoate as a white colored solid (95% yield, m.p.=170° C.). $^1$H-NMR (300 MHz, CDCl$_3$) δ 7.1 (d, 2H), 6.6 (t, 1H), 4.9 (s, OH), 3.9 (s, OCH$_3$).

Example 5

Synthesis of methyl 3,5-bis-dodecyloxybenzoate

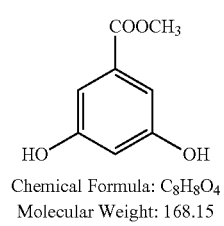

Chemical Formula: C$_8$H$_8$O$_4$
Molecular Weight: 168.15

+

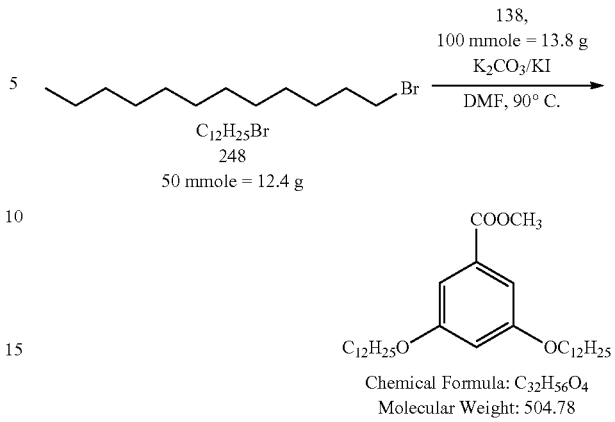

C$_{12}$H$_{25}$Br
248
50 mmole = 12.4 g 138,
100 mmole = 13.8 g
$\xrightarrow{\text{K}_2\text{CO}_3/\text{KI}}{\text{DMF, 90° C.}}$ Chemical Formula: C$_{32}$H$_{56}$O$_4$
Molecular Weight: 504.78

Methyl 3,5-dihydroxybenzoate (4.2 g, 25 mmol) was dissolved in 25 mL of dry DMF and then 13.86 g (100 mmol) of K$_2$CO$_3$ was added in the reaction mixture, where the above mixture was stirred at 80° C. for 1 h under a N$_2$ atmosphere and then 1-bromododecane (12.4 g, 50 mmol) was added dropwise to the reaction mixture. The reaction mixture was stirred at 90° C. for 24 h under N$_2$. At the end of the reaction, the mixture was poured onto ice, 2N—HCl and extracted with MC, H$_2$0, NaHCO$_3$ and brine. The solvent was removed in vacuo. The crude solid was purified by column chromatograph with 10% EA and hexane to yield 75% of the product. $^1$H-NMR (300 MHz, CDCl$_3$) δ 7.1 (d, 2H), 6.6 (t, 1H), 4.0 (t, 4H), 3.9 (s, OCH$_3$), 1.7-1.8 (m, 4H), 1.4-1.6 (m, 4H), 1.1-1.3 (m, 32H), 0.9 (t, 6H).

Example 6

Synthesis of 3,5-bis-dodecyloxybenzoic acid

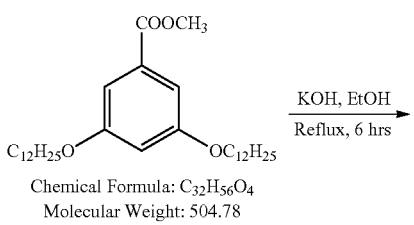

Chemical Formula: C$_{32}$H$_{56}$O$_4$
Molecular Weight: 504.78

$\xrightarrow{\text{KOH, EtOH}}{\text{Reflux, 6 hrs}}$

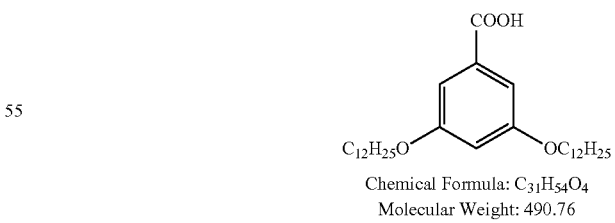

Chemical Formula: C$_{31}$H$_{54}$O$_4$
Molecular Weight: 490.76

Methyl 3,5-bis-dodecyloxybenzoate (8 g) was refluxed for 6 h with EtOH (25 mL) and 10% KOH. Then, the mixture was cooled and poured onto ice H$_2$O and extracted with MC, then the organic layer was stored over dry MgSO$_4$. The solvent was removed; the crude was recrystallized in EtOH to yield 85% of the benzoic acid product as a white solid. $^1$H-NMR (300 MHz, CDCl$_3$) δ 7.1 (d, 2H), 6.6 (t, 1H), 4.0 (t, 4H), 1.7-1.8 (m, 4H), 1.4-1.6 (m, 4H), 1.2-1.3 (m, 32H), 0.9 (t, 6H).

Example 7

Synthesis of N,N'-bis(2,6-diisopropylphenyl)-1-bromo-7-(iminohexyl-3,5-bis-dodecyloxybenzoate)perylene-3,4,9,10-tetracarboxydiimide

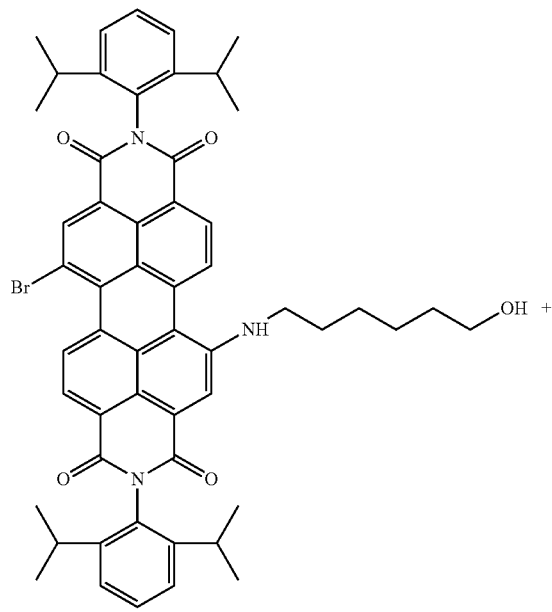

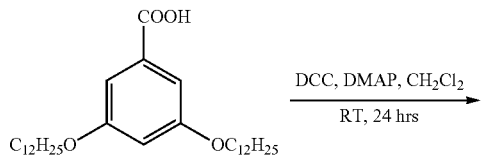

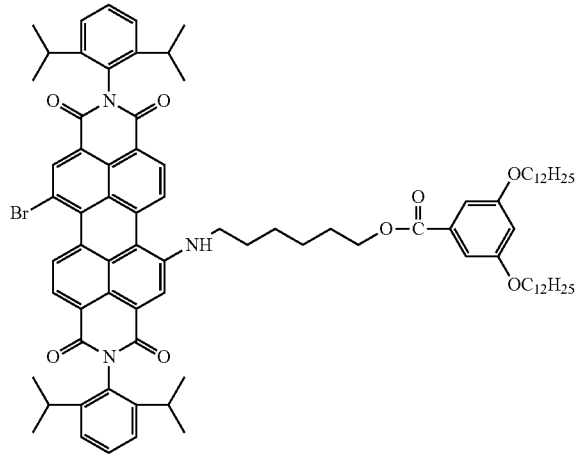

Bromo-6-hydroxyhexylaminoperylene bisimide (0.27 g, 0.3 mmol) was dissolved in 20 mL of CH$_2$Cl$_2$ and 3,5-bis-dodecyloxybenzoic acid (0.2 g, 0.4 mmol), DCC (0.31 g, 1.5 mmol), and DMAP (0.12 g, 1 mmol) were added. The reaction mixture was stirred at RT for 24 h under N$_2$. At the end of the reaction, the mixture was poured into 2N—HCl and then filtered. The organic layer was extracted with MC, washed with water and then the organic extract was stored over MgSO$_4$. The solvent was removed by rotary evaporation and the residue was purified by a column (silica gel, 20% ethyl acetate in n-hexane) to provide (90%) of the product as an green solid. $^1$H-NMR (300 MHz, CDCl$_3$) δ 9.48 (d, 1H), 9.02 (s, 1H), 8.81 (d, 1H), 8.70 (d, 1 H), 8.52 (d, 1H), 8.31 (s, 1H), 7.48 (t, 2H), 7.33 (d, 4H), 7.10 (d, 2H), 6.58 (t, 1H), 6.08 (br, NH), 4.28 (t, 2H), 3.84 (t, 4H), 3.5 (t, 2H), 2.62-2.8 (septet, 4H), 1.7-1.8 (m, 6H), 1.38-1.44 (m, 6H), 1.22-1.34 (m, 36H), 1.14-1.20 (d, 24H), 0.84-0.9 (t, 6H).

Example 8

Synthesis of Bithiophene

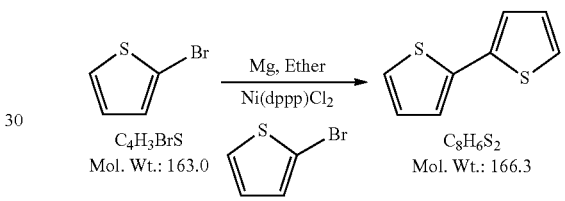

Gringard reagent 2-thiophenylmanesium bromide was prepared from 60 g of 2-bromothiophene (0.368 mole) and magnesium (9.7 g, 0.404 mole). Magnesium was slowly added to a mixture of 2-bromothiophene (50 g, 0.307 mole), Ni(dppp)Cl$_2$ (1.66 g, 3 mmol) in 150 mL dry ether at 0° C. The mixture was warmed to RT for 20 h before being quenched by diluted HCl. The aqueous layer was extracted with ether and all organic layers were combined. The solvent was evaporated after drying over MgSO$_4$. The crude liquid product was redistilled under reduced pressure to afford 40 g (80%) of a low melting solid of the tilled compound. Mp 32-33° C. $^1$H-NMR (300 MHz, CDCl$_3$) δ 7.19 (dd, 4H), 7.04 (t, 2H).

Example 9

Synthesis of 2-bithiophenyl borate

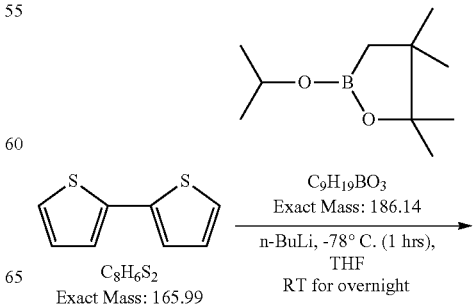

-continued

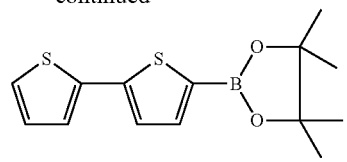

C₁₄H₁₇BO₂S₂
Exact Mass: 292.08
2-Isopropoxy-4,4,5,5-tetramethyl-[1,3,2]dioxaborolane Bithiophene (5 g, 30 mmol) was dissolved in 100 mL of dry THF. The mixture is stirred at −78° C. and n-BuLi (20.6 mL, 33 mmol) is added to the reaction mixture. The reaction mixture was stirred at RT for 1 h. The 2-isopropoxy-4,4,5,5-tetramethyl-1,3,2-dioxaborolane (6.7 g, 36 mmol) was added to the mixture at −78° C. and then the resulting mixture was stirred at −78° C. for 1 h and warmed to RT and stirred overnight. At the end of the reaction, the mixture was poured into water and extracted with ether and dried over MgSO₄. The solvent was removed and the crude product was purified by column chromatography (5% EA and hexane) to yield 40% of the product as a yellow colored liquid. ¹H-NMR (300 MHz, CDCl₃) δ 7.52 (d, 2H), 7.22-7.26 (m, 3H), 7.0-7.4 (dd, 1H), 1.3 (s, 12H).

Example 10

Synthesis of N,N'-bis(2,6-diisopropylphenyl)-1-bithiophene-7-(iminohexyl-3,5-bis-dodecyloxybenzoate)perylene-3,4,9,10-tetra carboxydiimide (SP2T)

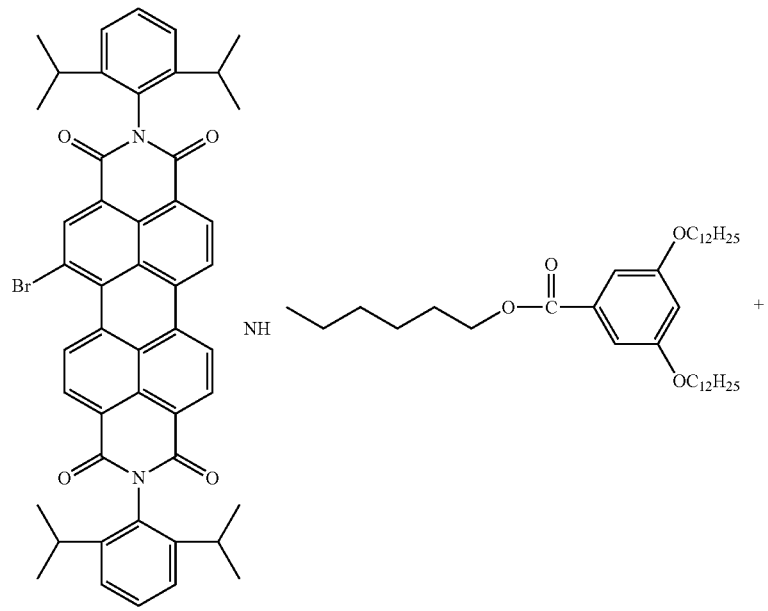

A
0.2 mmole = 0.275 g
Chemical Formula: C₈₅H₁₀₆BrN₃O₈
Molecular Weight: 1377.67

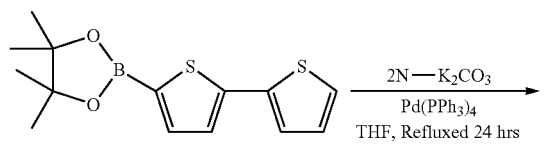

B
Chemical Formula: C₁₄H₁₇BO₂S₂
Molecular Weight: 292.22

0.4 mmole = 0.117

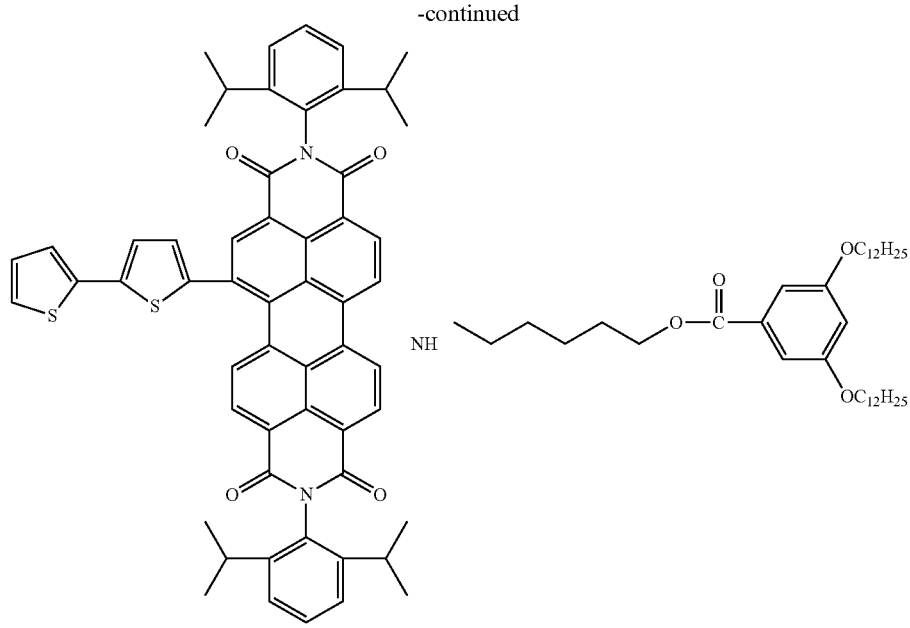

Chemical Formula: $C_{93}H_{111}N_3O_8S_2$
Molecular Weight: 1463.02

The starting monobromo-substituted perylene bisimide ester (0.275 g, 0.2 mmol) was dissolved in 25 mL of dry THF. A solution of 2N $K_2CO_3$ (3 mL) and 2 mol % (0.005 g) tetrakis(triphenylphosphine) palladium(0) were added into the reaction mixture, and then 0.117 g (0.4 mmol) of bithiophene borate was added. The resulting reaction mixture was refluxed for 24 h in $N_2$ before being poured into water and 2N—HCl. The aqueous layer was extracted with MC and the organic extracts were dried over magnesium sulfate. The solvent was removed by rotary evaporation and the residue was purified by a column (silica gel, 20% EA and n-hexane) to yield 85% of the product as a green solid. $^1$H-NMR (300 MHz, $CDCl_3$) δ 8.96 (d, 1H), 8.76 (s, 1H), 8.68 (d, 1H), 8.37 (d, 1H), 8.29 (s, 1H), 8.12 (d, 1H), 7.48-7.56 (m, 2H), 7.33-7.39 (m, 4H), 7.28 (dd, 2H), 7.22 (d, 1H), 7.18 (dd, 1H) 7.12 (d, 2H), 7.02 (dd, 1H), 6.58 (t, 1H), 6.0 (br, NH), 4.28 (t, 2H), 3.88 (t, 4H), 3.5 (t, 2H), 2.66-2.82 (septet, 4H), 1.7-1.8 (m, 6H), 1.38-1.44 (m, 6H), 1.22-1.34 (m, 36H), 1.14 (d, 24H), 0.82 (t, 6H).

Example 11

Synthesis of 2-hexylthiophene

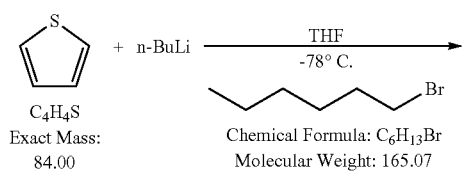

To a solution of thiophene (15 g, 0.178 mole) in 200 mL of dry THF at −78° C., n-BuLi (103 mL, 0.165 mol, 1.6M hexane) was added. The reaction mixture was warmed to RT and stirred for 1 h. After the mixture was cooled to −78° C., 23.15 mL (0.165 mole) of 1-bromohexane was added. The solution was warmed from −78° C. to RT and was stirred overnight. At the end of the reaction, the mixture was poured into ice water, the aqueous layer was extracted with ether, and the organic layer was dried over anhydrous $MgSO_4$. The solvent was removed by rotary evaporation. The residue was redistilled under vacuum to get a colorless liquid (yield=75%). $^1$H-NMR (300 MHz, $CDCl_3$) δ 7.12 (dd, 1H), 6.92-6.97 (m, 1H), 6.8 (dd, 1H). 2.8 (t, 2H), 1.6-1.9 (q, 2H), 1.30-1.49 (m, 6H), 0.82 (t, 3H).

Example 12

Synthesis of 2-hexyl-5-thiopheneborate

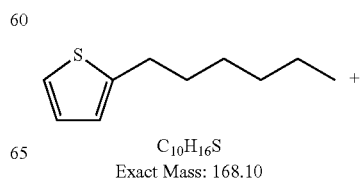

To a solution of 2-hexylthiophene (5 g, 29.76 mmol) in 50 mL of dry THF at −78° C., n-BuLi (13.2 mL, 33 mmol, 2.5 M hexane) was added. The reaction mixture was warmed to RT

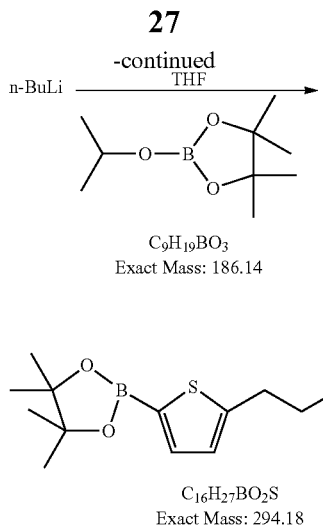

and stirred for 1 h. After the mixture was cooled to −78° C., 6.7 g (36 mmol) of 2-isopropoxy-4,4,5,5-tetramethyl-1,3,2-dioxaborolane was added. The solution was warmed from −78° C. to RT and was stirred overnight. At the end of the reaction, the mixture was poured into ice water, the aqueous layer was extracted with ether, and the organic layer was dried over anhydrous MgSO$_4$. The solvent was removed by rotary evaporation. The residue was distilled under vacuum. $^1$H-NMR (300 MHz, CDCl$_3$) δ 7.45 (d, 1H), 6.84 (d, 1H), 2.70 (t, 2H), 1.64-1.68 (q, 2H), 1.22-1.41 (m, 18), 0.84 (t, 3H).

Example 13

Synthesis of 2-hexylbithiophene

2-Bromothiophene (1.63 g, 10 mmol) was dissolved in 25 mL dry THF and a solution of 2N K$_2$CO$_3$ (5 mL) was added to the reaction mixture. And then 2 mol % (0.115 g) tetrakis (triphenylphosphine) palladium(0) and 2-hexyl-5-thiophene borate (2.94 g, 10 mmol) were added to the reaction mixture. The reaction mixture was refluxed for 24 h in N$_2$. Before being poured into water and 2N—HCl, the aqueous layer was extracted with MC and the organic extracts were dried over magnesium sulfate. The solvent was removed by rotary evaporation and the residue was purified by a column (silica gel, 5% EA and n-hexane) to yield 90% of the product as a yellow liquid. $^1$H-NMR (300 MHz, CDCl$_3$) δ 7.18 (dd, 1H), 7.12 (dd, 1H), 7.0-7.04 (m, 2H), 6.71 (dd, 1H), 2.78 (t, 2H), 1.68-1.78 (q, 2H), 1.32-1.46 (m, 6H), 0.84 (t, 3H).

Example 14

Synthesis of 2-hexylbithiopheneborate

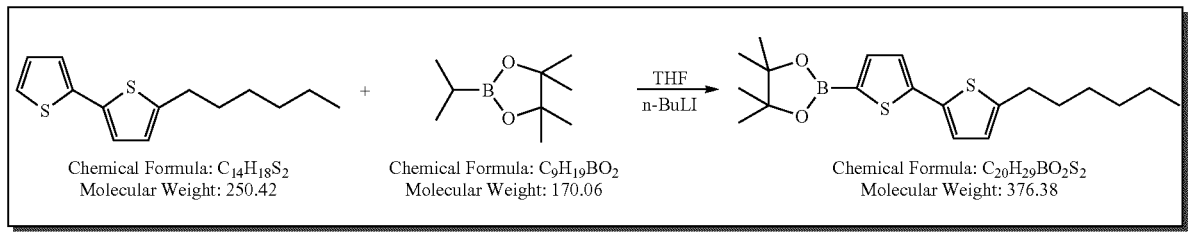

2-Hexylbithiophene (5 g, 20 mmol) was dissolved in 100 mL of dry THF and the mixture is stirred at −78° C. After addition of n-BuLi (20.6 mL, 33 mmol) the reaction mixture was stirred at RT for 1 h and 2-isopropoxy-4,4,5,5-tetramethyl-1,3,2-dioxaborolane (5.6 g, 30 mmol) was added into the mixture at −78° C. The resulting mixture was stirred at −78° C. for 1 h, warmed to RT and stirred overnight. At the end of the reaction the mixture is poured into water and extracted with ether and dried with MgSO$_4$. The solvent was removed and the crude product was purified by column chromatography (5% EA and hexane) to get 40% of the title product as a deep blue colored liquid. $^1$H-NMR (300 MHz,

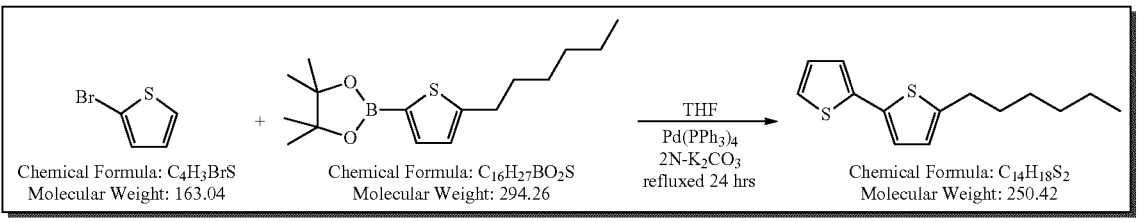

CDCl$_3$) δ 7.52 (dd, 1H), 7.22 (dd, 1H), 7.0 (dd, H), 6.68 (dd, 1H), 2.76 (t, 2H), 1.62-1.74 (q, 2H), 1.24-1.40 (m, 18H), 0.84 (t, 3H).
Example 15
Synthesis of N,N'-bis(2,6-diisopropylphenyl)-1-n-hexylbithiophene-7-(iminohexyl-3,5-bis-dodecyloxybenzoate)perylene-3,4,9,10-tetra carboxydiimide (SP2TH)
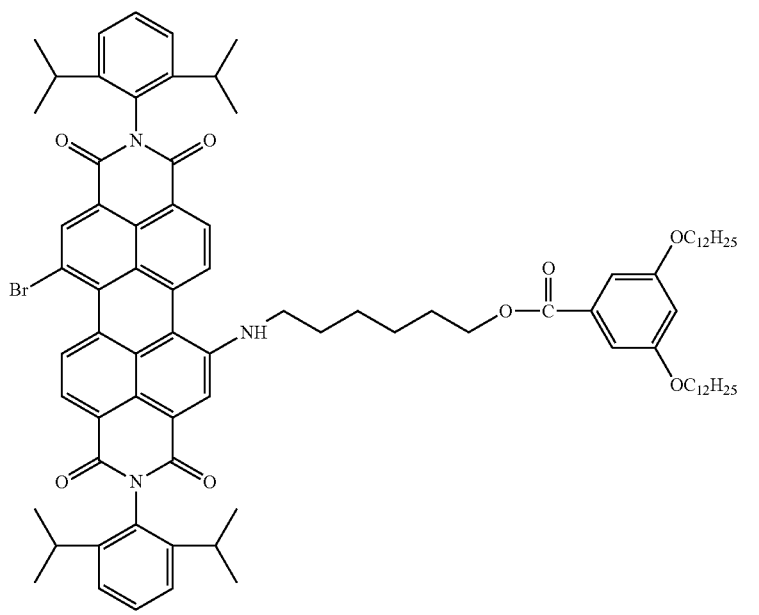
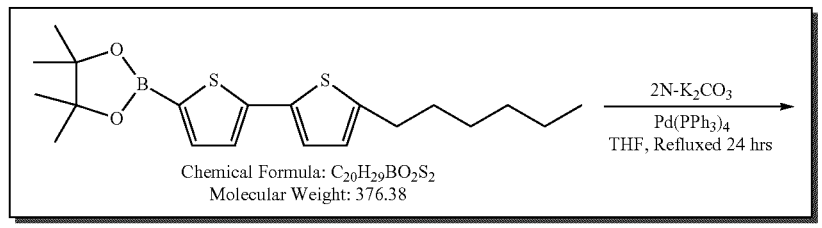

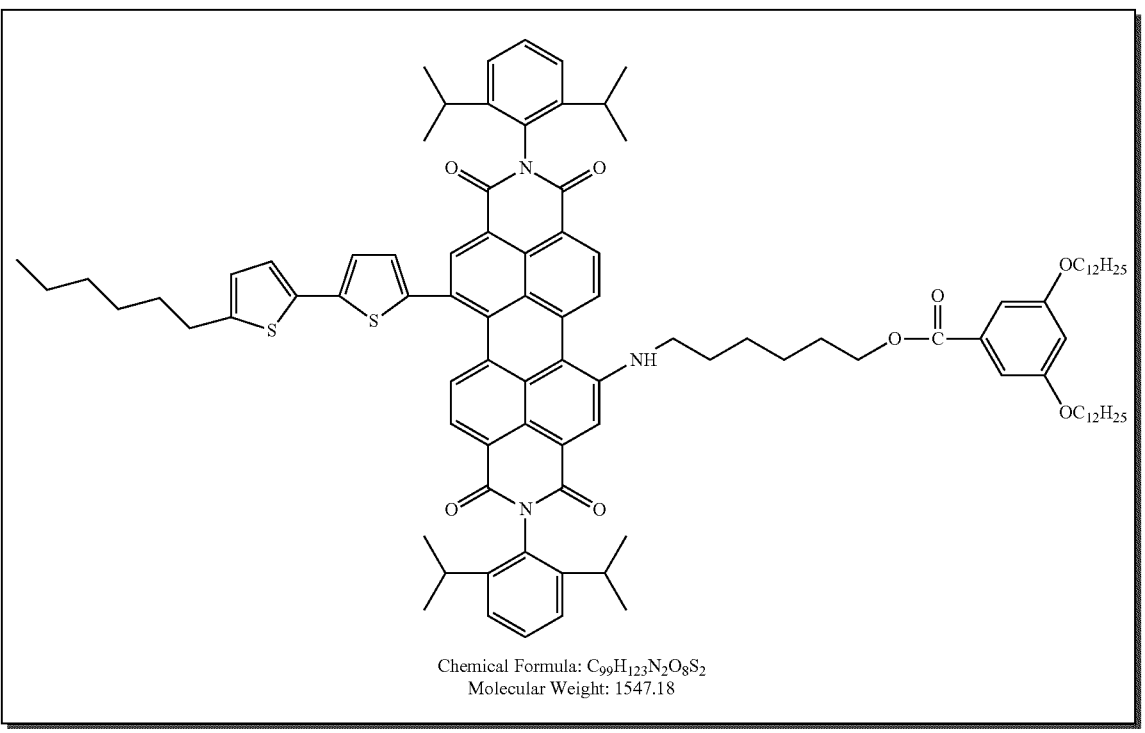

Chemical Formula: C99H123N2O8S2
Molecular Weight: 1547.18

The starting monobromo-substituted perylene bisimide ester (0.275 g, 0.2 mmol) was dissolved in 25 mL dry THF. A solution of 2N $K_2CO_3$ (3 mL) and 2 mol % (0.005 g) tetrakis(triphenylphosphine) palladium(0) were added to the reaction mixture and then 0.150 g (0.4 mmol) of 2-hexylbithiophene borate was added. The reaction mixture was refluxed for 24 h in $N_2$ before being poured into water and acidifying with 2N—HCl. The aqueous layer was extracted with MC and the organic extracts were dried over magnesium sulfate. The solvent was removed by rotary evaporation and the residue was purified by a column (silica gel, 20% EA and n-hexane) to yield 81% of the product as a green solid. $^1$H-NMR (300 MHz, CDCl$_3$) δ 8.92 (d, 1H), 8.76 (s, 1H), 8.66 (d, 1H), 8.36 (d, 1H), 8.30 (s, 1H), 8.12 (d, 1H), 7.44-7.51 (m, 2H), 7.32-7.38 (m, 4H), 7.26 (dd, 1H), 7.22 (d, 1H), 7.12 (d, 2H), 6.98 (d, 1H), 6.68 (d, 1H), 6.60 (t, 1H), 6.02-6.07 (br, NH), 4.28 (t, 2H), 3.88 (t, 4H), 3.52 (t, 2H), 2.66-2.82 (septet, 6H), 1.7-1.8 (m, 8H), 1.38-1.44 (m, 8H), 1.22-1.34 (m, 40H), 1.14 (d, 24H), 0.82 (t, 9H).

Example 16

Synthesis of N,N'-bis(2,6-diisopropylphenyl)-1-bromobithiophene-7-(iminohexyl-3,5-bis-dodecyloxybenzoate)perylene-3,4,9,10-tetracarboxydiimide

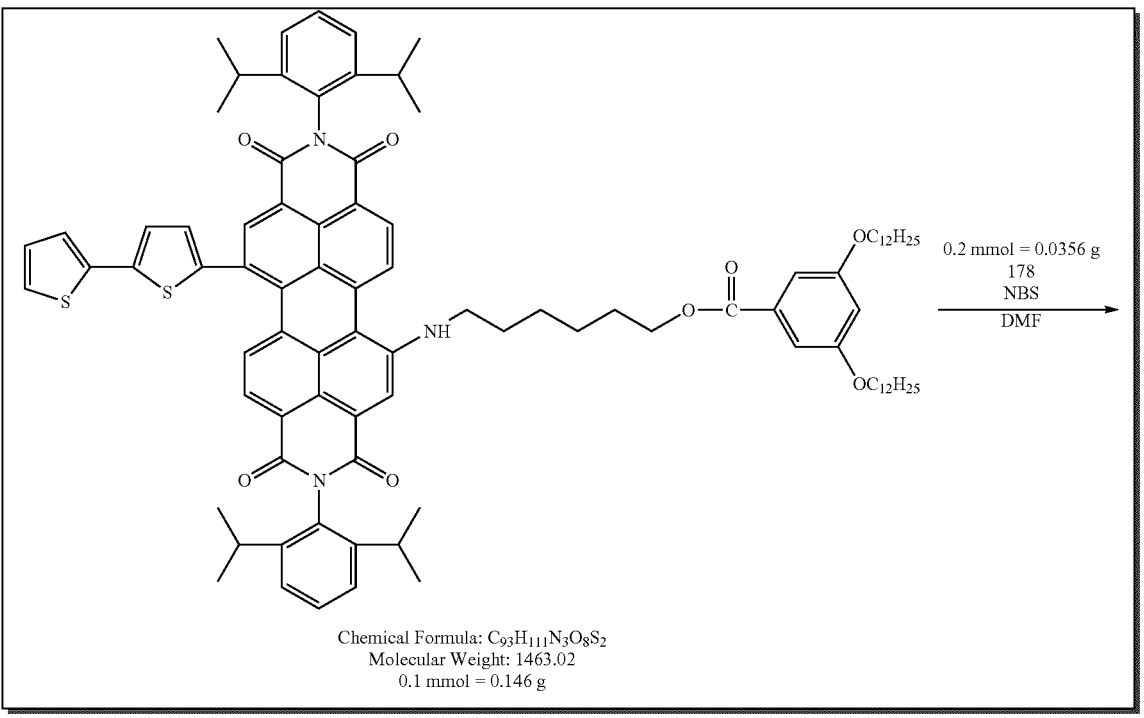

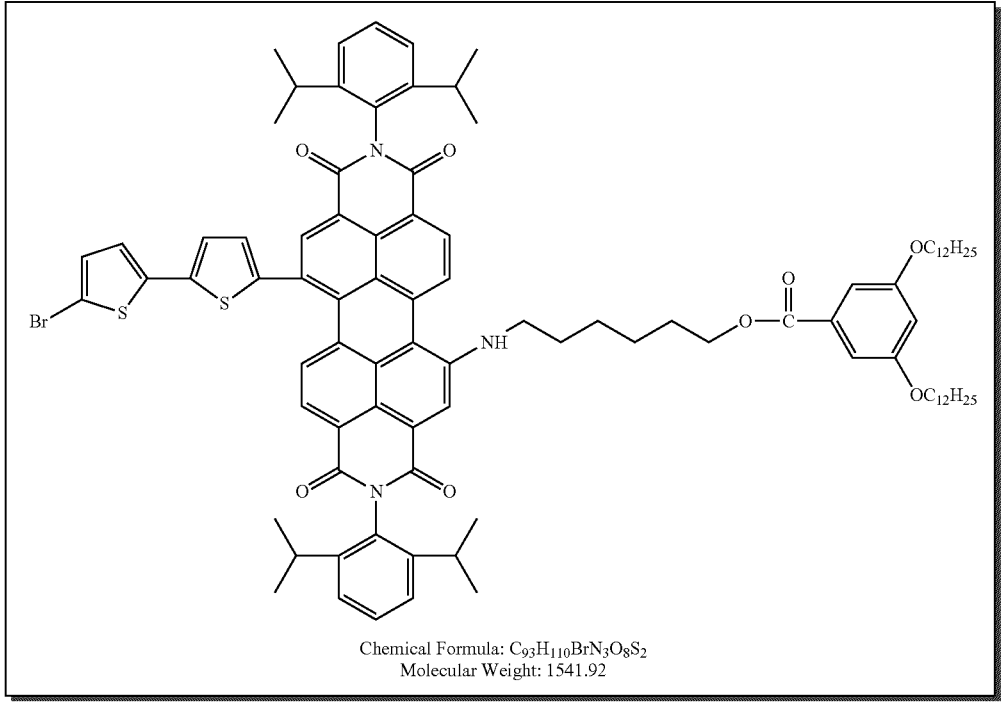

To a solution of perylene bithiophene bisimide ester (0.292 g, 0.2 mmol) in 10 mL of dry DMF under nitrogen in the dark, a solution of NBS (0.0356 g, 0.2 mmol) in DMF (3 mL) was added dropwise at 0° C. The resulting green solution was stirred at RT under nitrogen overnight and the reaction mixture was poured onto the crushed ice. The reaction mixture was extracted with MC, washed with water and 2N—HCl solution and then the organic extract was stored over $MgSO_4$. The solvent was removed by a rotary evaporator; the crude solid was purified by a column in 10% EA and hexane to obtain the product (78%) as a green colored solid. $^1$H-NMR (300 MHz, $CDCl_3$) δ 8.92 (d, 1H), 8.76 (s, 1H), 8.68 (d, 1H), 8.34 (d, 1 H), 8.30 (s, 1H), 8.12 (d, 1H), 7.44-7.54 (m, 2H), 7.34-7.38 (m, 4H), 7.21 (d, 1H), 7.12-7.18 (m, bithiophene 1H and Ar 2H), 6.98 (d, 1H), 6.92 (d, 1H), 6.58 (t, 1H), 6.02 (br, NH), 4.28 (t, 2H), 3.88 (t, 4H), 3.52 (t, 2H), 2.66-2.82 (septet, 4H), 1.7-1.8 (m, 6H), 1.38-1.44 (m, 6H), 1.22-1.34 (m, 36H), 1.14 (d, 24H), 0.83 (t, 6H).

Example 17

Synthesis of 2-thiopheneboronic acid

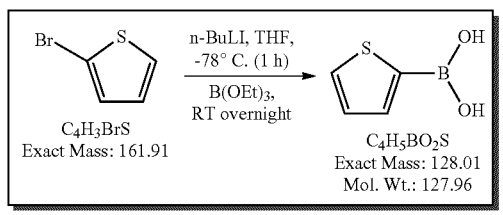

To a solution of 2-bromothiophene (8.05 g, 50 mmol) in 100 mL anhydrous THF at −78° C., n-BuLi (34 mL, 55 mmol, 1.6 M hexane) was added. The reaction mixture was warmed to RT and stirred for 1 h. After the mixture was cooled to −78° C., triethyl borate (17 mL, 100 mmol) was slowly added into the mixture and the solution was warmed to RT and stirred for 12 h. At the end of the reaction, the mixture was poured into the 100 mL of 2N HCl and ice, the aqueous layer was extracted with ether, and the organic layer was dried over anhydrous $MgSO_4$. The solvent was removed by rotary evaporation. The residue was recrystallized with n-hexane to obtain the product (45%). $^1$H-NMR (300 MHz, $CDCl_3$) δ 7.68 (dd, 1H), 7.3 (d, 1H), 7.15 (dd, 1H).

Example 18

Synthesis of N,N'-bis(2,6-diisopropylphenyl)-1-terthiophene-7-(iminohexyl-3,5-bis-dodecyloxybenzoate)perylene-3,4,9,10-tetra carboxydiimide (SP3T)

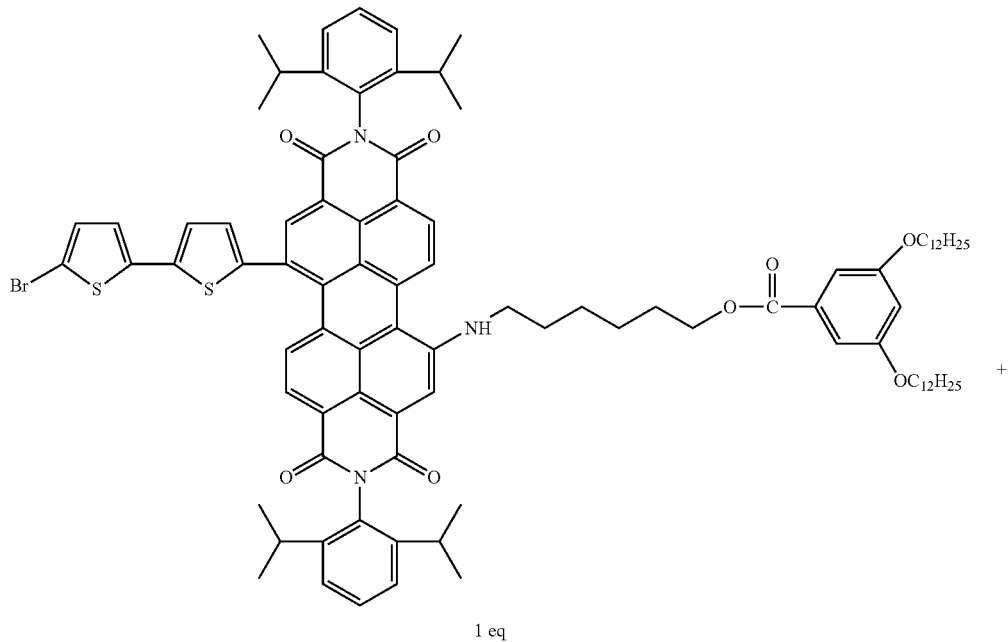

1 eq

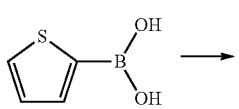

3 eq

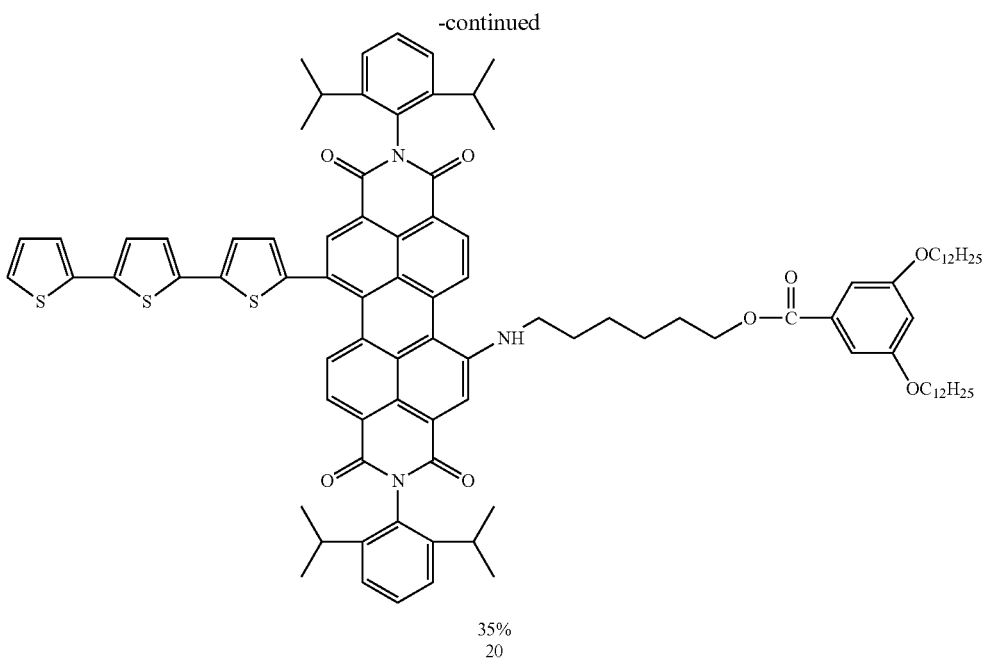

35%
20

The perylene bromobithiophene bisimide ester (0.77 g, 0.5 mmol) was dissolved in 25 mL dry THF. A solution of 2N K$_2$CO$_3$ (3 mL) and 2 mol % (12 mg) tetrakis(triphenylphosphine) palladium(0) were added into the reaction mixture, and then thiopheneboronic acid (0.192 g, 1.5 mmol) was added. The reaction mixture was refluxed for 24 h under N$_2$, before being poured into water and acidifying with 2N—HCl. The aqueous layer was extracted with MC and the organic extracts were dried over magnesium sulfate. The solvent was removed by rotary evaporation and the residue was purified by a column (silica gel, 20% EA and n-hexane) to yield 35% of the product as a green solid. $^1$H-NMR (300 MHz, CDCl$_3$) δ 8.92 (d, 1H), 8.76 (s, 1H), 8.66 (d, 1H), 8.36 (d, 1H), 8.30 (s, 1H), 8.12 (d, 1H), 7.44-7.54 (m, 2H), 7.32-7.38 (m, 4H), 7.26 (dd, 2H), 7.22 (d, 1H), 7.18 (d, 1H), 7.12 (d, 2H), 6.98-7.01 (t, 2H), 6.54 (d, 1H), 6.52 (t, 1H), 6.02 (br, NH), 4.28 (t, 2H), 3.88 (t, 4H), 3.52 (t, 2H), 2.66-2.82 (septet, 4H), 1.7-1.82 (m, 8H), 1.38-1.44 (m, 8H), 1.22-1.34 (m, 32H), 1.14 (d, 24H), 0.82 (t, 6H). $^{13}$C-NMR (300 MHz, CDCl$_3$) δ166.74 (C=O), 163.81, 163.72, 163.65, 160.38, 156.46, 147.58, 145.90, 143.16, 139.67, 137.27, 137.09, 136.89, 136.53, 135.59, 135.05, 132.62, 132.27, 132.02, 131.36, 131.01, 130.87, 130.42, 130.33, 130.18, 129.80, 128.343, 128.13, 126.52, 125.00, 124.76, 124.67, 124.25, 124.2, 123.22, 122.69, 121.37, 120.29, 119.59, 115.61, 107.97, 106.44, 100.34, 86.73, 76.80, 68.271, 65.02, 45.03, 33.65, 32.12, 31.23, 29.86, 29.84, 29.80, 29.78, 29.58, 29.54, 29.45, 29.41, 28.86, 27.09, 26.23, 25.99, 24.29, 24.22, 22.88, 14.30.

Example 19

Synthesis of 2-hexylterthiophene

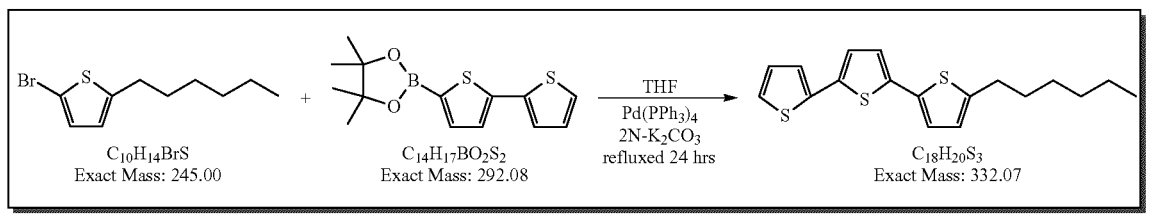

2-Bromo-5-hexylthiophene (1.22 g, 5 mmol) was dissolved in 25 mL dry THF. A solution of 2M K$_2$CO$_3$ (5 mL) and 2 mol % (0.115 g) tetrakis(triphenylphosphine) palladium(0) were added into the reaction mixture and then bithiophene borate (1.46 g, 5 mmol) was added. The reaction mixture was refluxed for 24 h in N$_2$ before being poured into water and 2N—HCl. The aqueous layer was extracted with MC and the organic extracts were dried over magnesium sulfate. The solvent was removed by rotary evaporation and the residue was purified by a column (silica gel, in n-hexane) to yield 80% of the product as a yellow solid. $^1$H-NMR (300 MHz, CDCl$_3$) δ 7.19-7.22 (dd, 1H), 7.12-7.16 (dd, 1H), 7.06-7.08 (d, 1H), 7.02-7.04 (d, 1H), 6.97-7.00 (m, 2H), 6.67-6.69 (d, 1H). 2.78-2.82 (t, 2H), 1.64-1.74 (q, 2H), 1.24-1.44 (m, 6H), 0.84-0.94 (t, 3H).

Example 20

Synthesis of 2-hexylterthiopheneborate

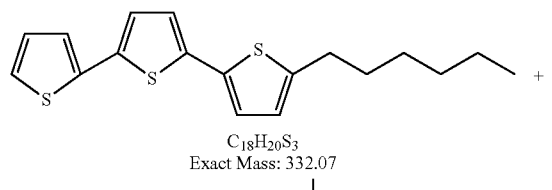

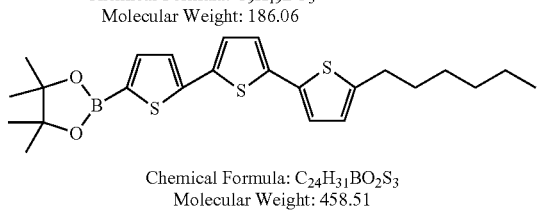

2-Hexylterthiophene (3.32 g, 10 mmol) was dissolved in 50 mL of dry THF. The mixture was stirred at −78° C. and 4 mL (10 mmol) of n-BuLi was added into the reaction mixture. The reaction mixture was stirred at RT for 1 h and 2-isopropoxy-4,4,5,5-tetramethyl-1,3,2-dioxaborolane (2.79 g, 15 mmol) was added into the mixture at −78° C. Then the resulting mixture was stirred at −78° C. for 1 h and warmed to RT and stirred overnight. At the end of the reaction, the mixture was poured into water and extracted with ether and dried over $MgSO_4$. The solvent was removed and the crude product was purified by column chromatography (5% EA and hexane) to yield 35% of the product as a green solid. $^1$H-NMR (300 MHz, $CDCl_3$) δ 7.48 (dd, 1H), 7.20 (d, 1H), 7.1 (d, 1H), 7.0 (dd, 2H), 6.68 (d, 1H), 2.76 (t, 2H), 1.62-1.74 (q, 2H), 1.24-1.40 (m, 18H), 0.84 (t, 3H).

Example 21

Synthesis of N,N'-bis(2,6-diisopropylphenyl)-1-hexylterthiophene-7-(iminohexyl-3,5-bis-dodecyloxybenzoate)perylene-3,4,9,10-tetra carboxydiimide (SP3TH)

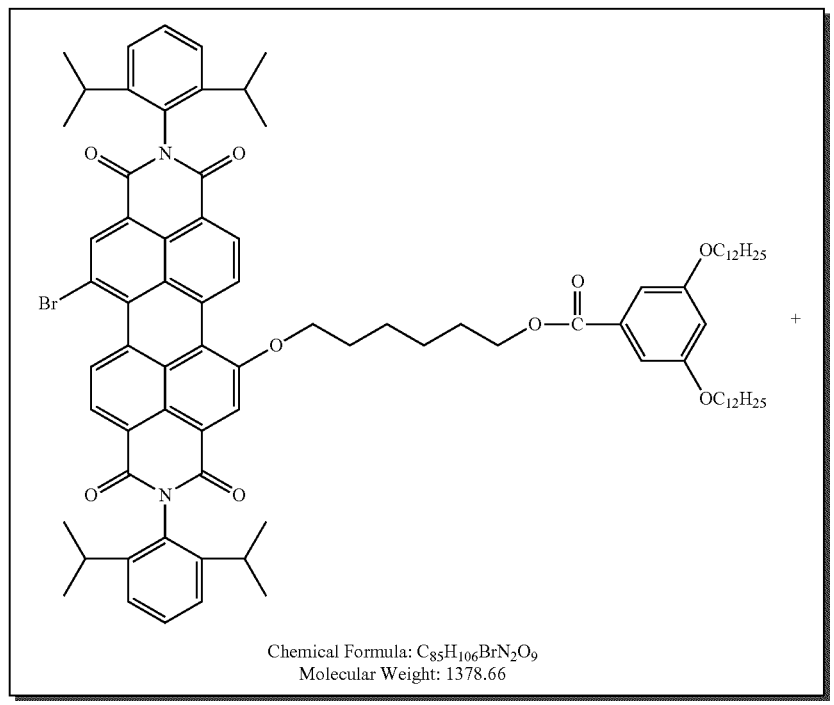

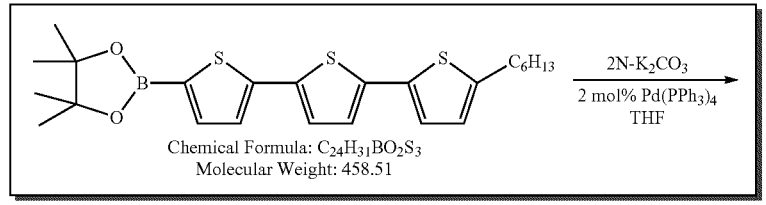

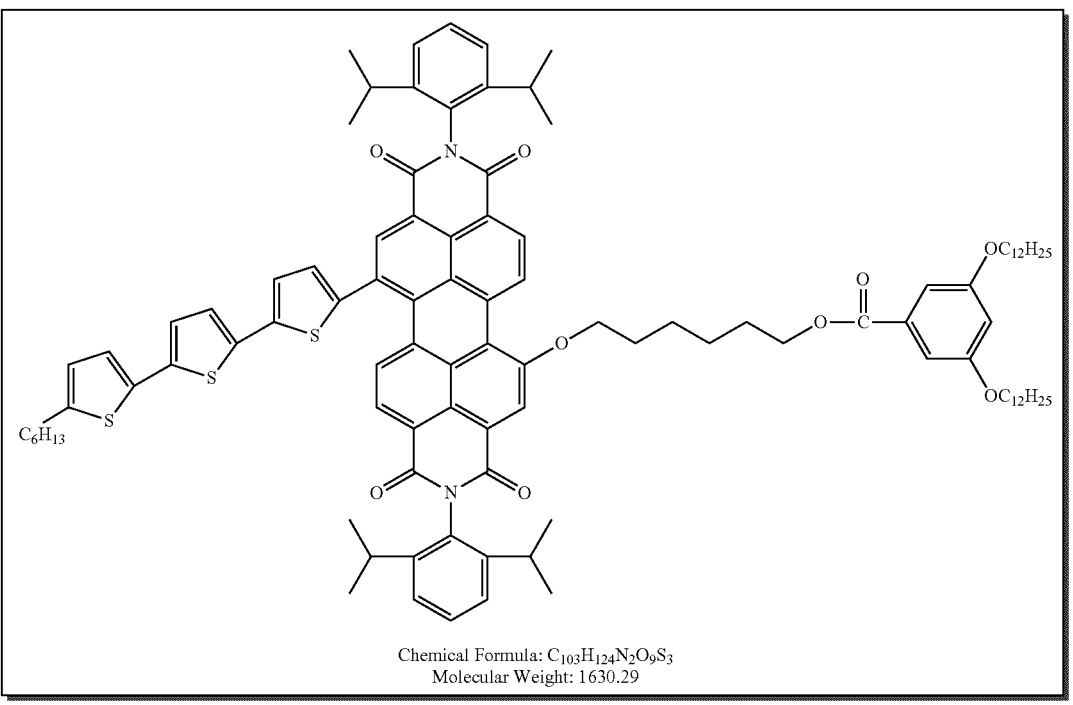

Chemical Formula: C$_{103}$H$_{124}$N$_2$O$_9$S$_3$
Molecular Weight: 1630.29

The bromo-perylene bisimide ester (1 g, 0.73 mmol) was dissolved in 25 mL dry THF and a solution of 2N K$_2$CO$_3$ (3 mL) was added into the reaction mixture. And then 2 mol % (12 mg) tetrakis(triphenylphosphine) palladium(0) and 2-hexylterthiophene borate (0.5 g, 1.08 mmol) were added into the reaction mixture. The reaction mixture was refluxed for 24 h in N$_2$ before being poured into water, and acidifying with 2N—HCl. The aqueous layer was extracted with MC and the organic extracts were dried over magnesium sulfate. The solvent was removed by rotary evaporation and the residue was purified by a column (silica gel, 20% EA and n-hexane) to yield 63% of the product as a green solid. $^1$H-NMR (300 MHz, CDCl$_3$) δ 8.92 (d, 1H), 8.76 (s, 1H), 8.66 (d, 1H), 8.36 (d, 1 H), 8.30 (s, 1H), 8.12 (d, 1H), 7.44-7.54 (m, 2H), 7.32-7.38 (m, 4H), 7.22 (d, 1H), 7.18 (d, 1H), 7.12 (d, 2H), 7.04 (d, 1H), 6.98 (t, 2H), 6.54 (d, 1H), 6.52 (t, 1H), 6.02 (br, NH), 4.28 (t, 2H), 3.88 (t, 4H), 3.52 (t, 2H), 2.66-2.82 (septet, 6H), 1.7-1.8 (m, 8H), 1.22-1.44 (m, 48H), 1.14 (d, 24H), 0.82 (t, 9H). $^{13}$C-NMR (300 MHz, CDCl$_3$) δ 166.74 (C=O), 163.81, 163.72, 163.65, 160.38, 156.46, 147.58, 145.90, 143.16, 139.67, 137.27, 137.09, 136.89, 136.53, 135.59, 135.05, 132.62, 132.27, 132.02, 131.36, 131.01, 130.87, 130.42, 130.33, 130.18, 129.80, 128.343, 128.13, 126.52, 125.00, 124.76, 124.67, 124.25, 124.2, 123.22, 122.69, 121.37, 120.29, 119.59, 115.61, 107.97, 106.44, 100.34, 86.73, 76.80, 68.271, 65.02, 45.03, 33.65, 32.12, 31.23, 29.86, 29.84, 29.80, 29.78, 29.58, 29.54, 29.45, 29.41, 28.86, 27.09, 26.23, 25.99, 24.29, 24.22, 22.88, 14.30.

Example 22
Synthesis of N,N'-bis(2,6-diisopropylphenyl)-1-quarterthiophene-7-(iminohexyl-3,5-bis-dodecyloxybenzoate)perylene-3,4,9,10-tetra carboxydiimide (SP4T)
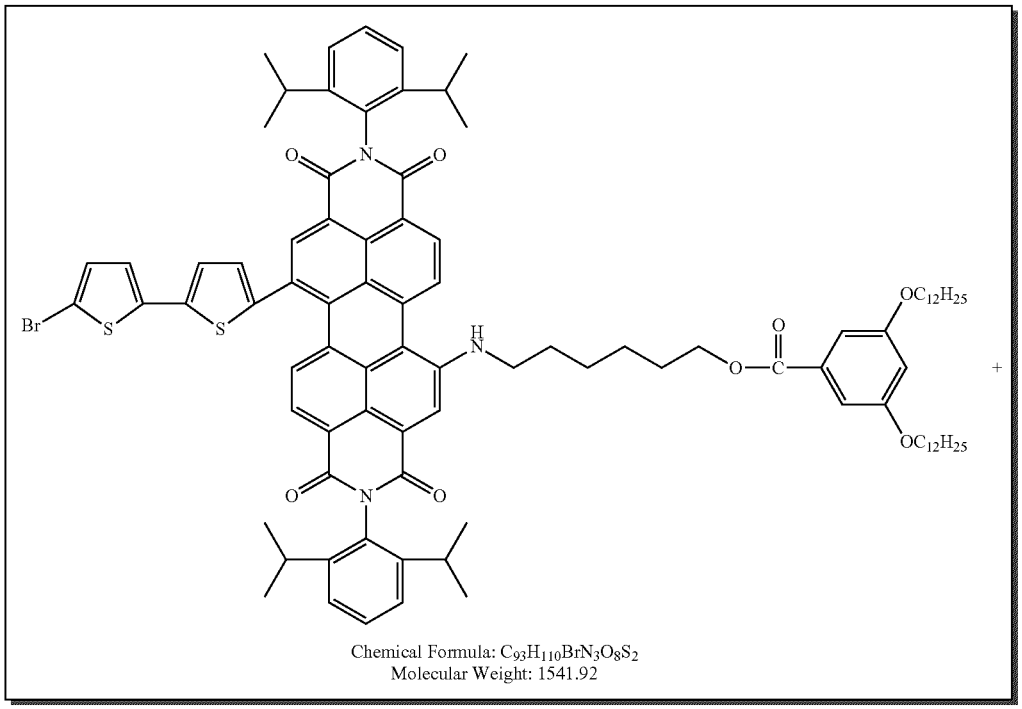
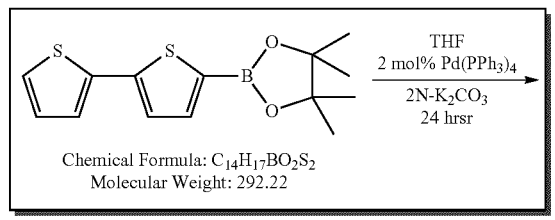

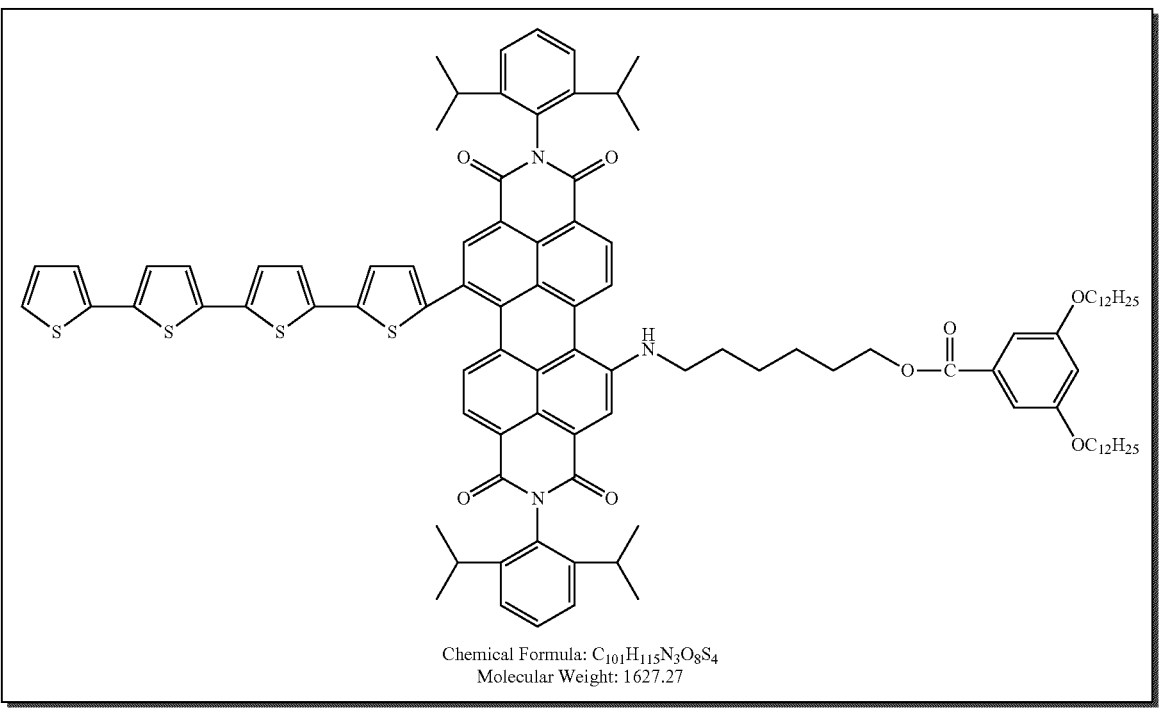

Chemical Formula: $C_{101}H_{115}N_3O_8S_4$
Molecular Weight: 1627.27

The perylene 2-bromobithiophene bisimide ester (0.308 g, 0.2 mmol) was dissolved in 25 mL dry THF and a solution of 2N $K_2CO_3$ (3 mL) was added into the reaction mixture. Then 2 mol % (0.005 g) tetrakis(triphenylphosphine) palladium(0) and 0.117 g (0.4 mmol) of bithiophene borate (0.117 g, 0.4 mmol) were added into the reaction mixture. The reaction mixture was refluxed for 24 h in $N_2$ before being poured into water, and acidifying with 2N—HCl. The aqueous layer was extracted with MC and the organic extracts were dried over magnesium sulfate. The solvent was removed by rotary evaporation and the residue was purified by a column (silica gel, 20% EA and n-hexane) to yield 50% of the product as a green solid. $^1$H-NMR (300 MHz, acetone $d_6$) δ 9.12 (d, 1H), 8.62 (s, 1H), 8.58 (d, 1H), 8.42 (d, 1H), 8.34 (s, 1H), 8.10 (d, 1H), 7.60-7.72 (m, 2H), 7.44-7.51 (m, 4H), 7.32-7.42 (m, 5H), 7.22 (d, 1H), 7.18 (d, 2H) 7.12 (d, 1H), 7.08 (d, 1H), 6.98 (d, 1H), 6.54 (t, 1H), 6.0 (br, NH), 4.24 (t, 2H), 3.82 (t, 4H), 3.62 (t, 2H), 2.82-2.84 (septet, 4H), 1.62-1.82 (m, 12H), 1.18-1.42 (m, 60H), 0.82 (t, 6H).

Example 23
Synthesis of N,N'-bis(2,6-diisopropylphenyl)-1-hexylquarterthiophene-7-(iminohexyl-3,5-bis-dodecyloxybenzoate) perylene-3,4,9,10-tetracarboxydiimide (SP4TH)
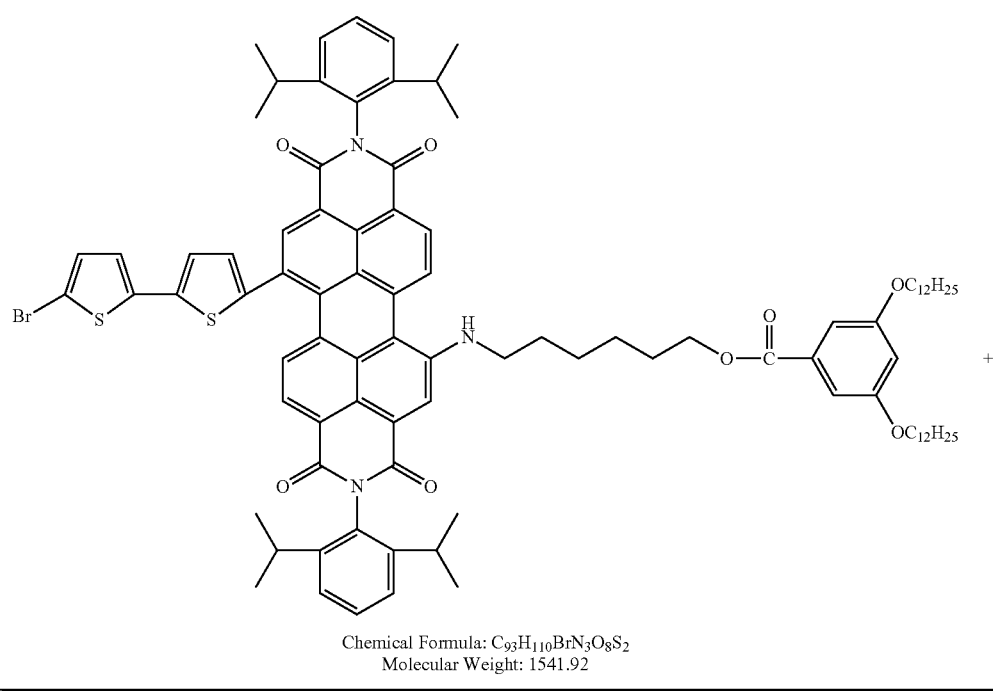
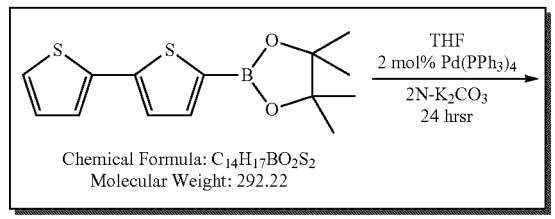

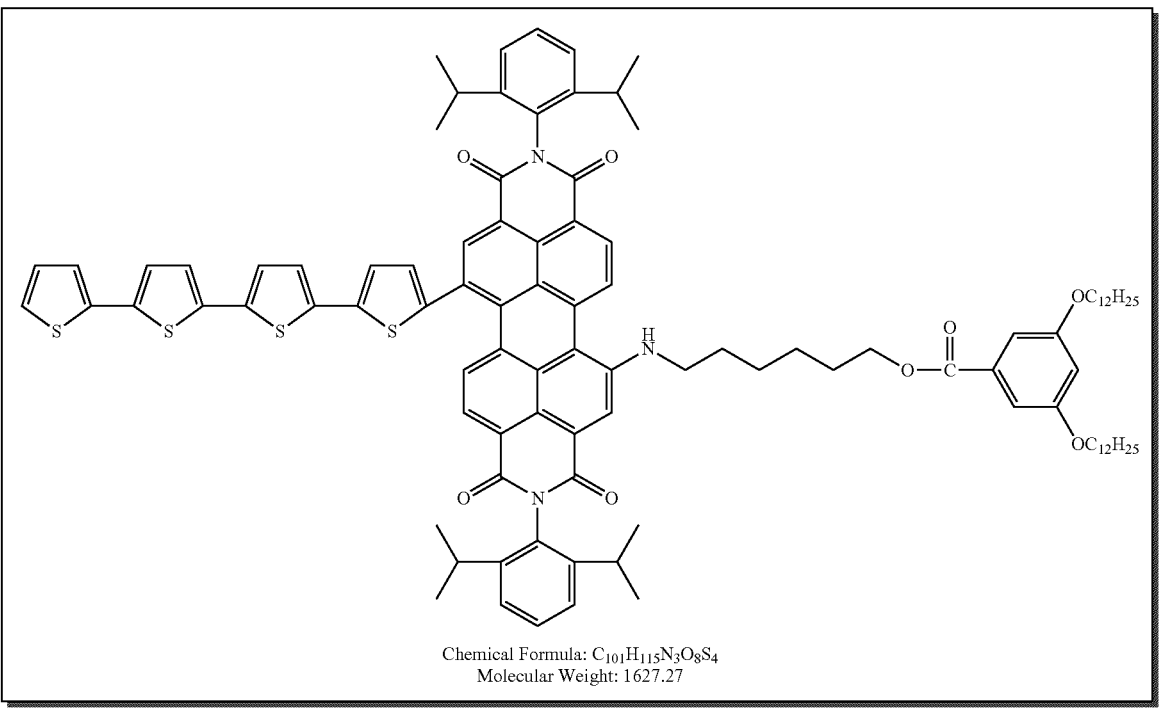

Chemical Formula: $C_{101}H_{115}N_3O_8S_4$
Molecular Weight: 1627.27

The perylene 2-bromobithiophene bisimide ester (0.308 g, 0.2 mmol) was dissolved in 25 mL dry THF and a solution of 2N $K_2CO_3$ (3 mL) was added into the reaction mixture. Then 2 mol % (0.005 g) tetrakis(triphenylphosphine) palladium(0) and hexylbithiophene borate (0.15 g, 0.4 mmol) were added into the reaction mixture. The reaction mixture was refluxed for 24 h in $N_2$ before being poured into water, and acidifying with 2N—HCl. The aqueous layer was extracted with MC and the organic extracts were dried over magnesium sulfate. The solvent was removed by rotary evaporation and the residue was purified by a column (silica gel, 20% EA and n-hexane) to provide (45%) of the product as a green solid. $^1$H-NMR (300 MHz, acetone $d_6$) δ 9.1 (d, 1H), 8.61 (s, 1H), 8.58 (d, 1H), 8.42 (d, 1H), 8.31 (s, 1H), 8.08 (d, 1H), 7.3-7.5 (m, 9H), 7.16 (d, 1H), 7.02-7.1 (m, 3H), 6.98 (d, 2H), 6.78 (d, 1H), 6.52 (t, 1H), 4.28 (t, 2H), 3.88 (t, 4H), 3.52 (t, 2H), 2.66-2.82 (septet, 6H), 1.62-1.72 (m, 8H), 1.21-1.34 (m, 48H), 1.10-1.20 (m, 24H), 0.80 (t, 9H).

Example 24
Synthesis of N,N'-bis(2,6-diisopropylphenyl)-1-pentathiophene-7-(iminohexyl-3,5-bis-dodecyloxybenzoate)perylene-3,4,9,10-tetra carboxydiimide (SP5T)
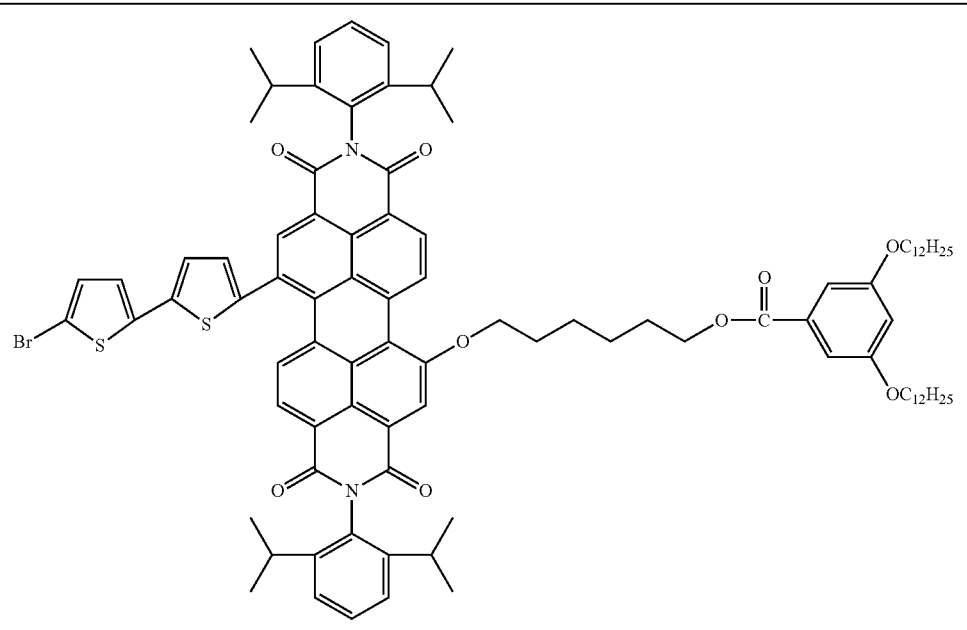
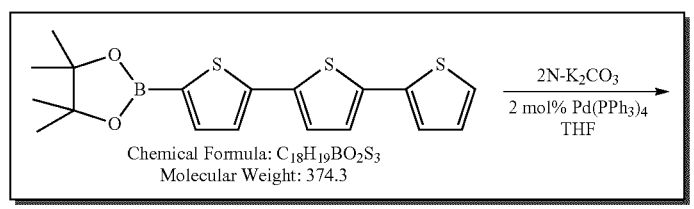

-continued

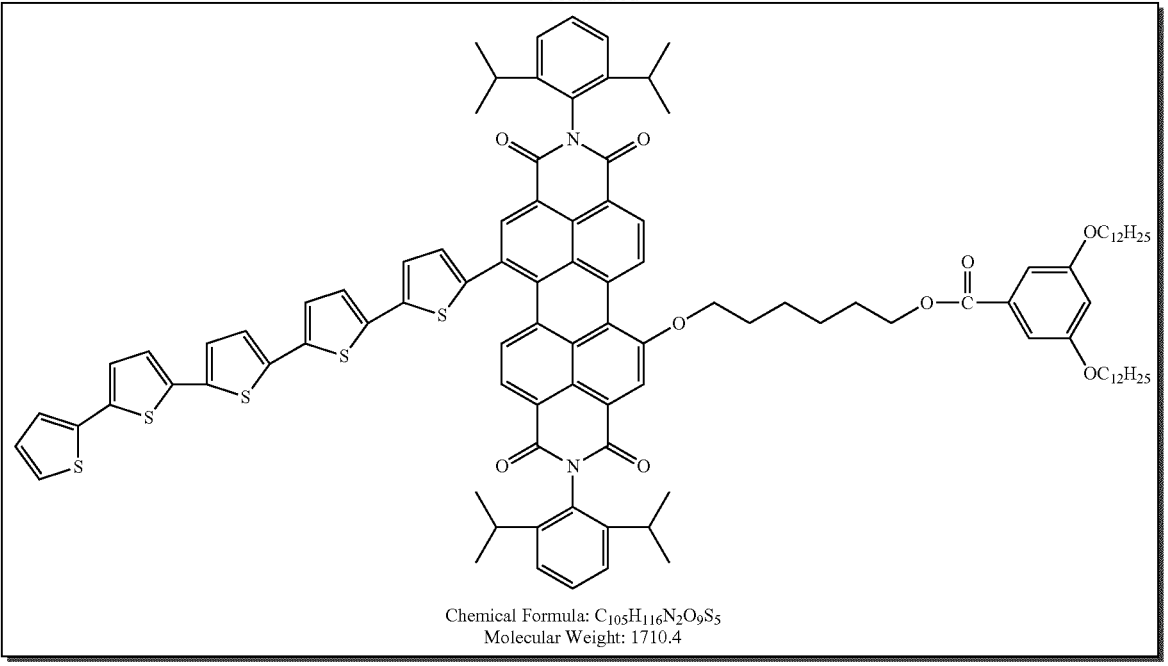

Chemical Formula: $C_{105}H_{116}N_2O_9S_5$
Molecular Weight: 1710.4

The perylene 2-bromobithiophene bisimide ester (0.308 g, 0.2 mmol) was dissolved in 25 mL dry THF and a solution of 2N $K_2CO_3$ (3 mL) was added into the reaction mixture. Then 2 mol % (0.005 g) tetrakis(triphenylphosphine) palladium(0) and terthiophene borate (0.15 g, 0.4 mmol) were added into the reaction mixture. The resulting reaction mixture was refluxed for 24 h in $N_2$ before being poured into water and acidifying with 2N—HCl. The aqueous layer was extracted with MC and the organic extracts were dried over magnesium sulfate. The solvent was removed by rotary evaporation and the residue was purified by a column (silica gel, 20% EA and n-hexane) to yield 49% of the product as a green solid. $^1$H-NMR (300 MHz, acetone $d_6$) δ 8.80 (d, 1H), 8.68 (s, 1H), 8.52 (d, 1H), 8.36 (d, 1 H), 8.29 (s, 1H), 8.12 (d, 1H), 7.44-7.54 (m, 2H), 7.3-7.38 (m, 4H), 7.20 (dd, 2H), 7.16 (d, 1H), 7.12 (d, 2H), 7.01-7.11 (m, 8H), 6.59 (t, 1H), 4.28 (t, 2H), 3.88 (t, 4H), 3.52 (t, 2H), 2.66-2.82 (septet, 4H), 1.7-1.8 (m, 8H), 1.38-1.44 (m, 8H), 1.22-1.34 (m, 32H), 1.14-1.20 (m, 24H), 0.82-0.92 (t, 6H). $^{13}$C-NMR (300 MHz, $CDCl_3$) δ 166.74 (C=O), 163.81, 163.72, 163.65, 160.38, 156.46, 147.58, 145.90, 143.16, 139.67, 137.27, 137.09, 136.89, 136.53, 135.59, 135.05, 132.62, 132.27, 132.02, 131.36, 131.01, 130.87, 130.42, 130.33, 130.18, 129.80, 128.343, 128.13, 126.52, 125.00, 124.76, 124.67, 124.25, 124.2, 123.22, 122.69, 121.37, 120.29, 119.59, 115.61, 107.97, 106.44, 100.34, 86.73, 76.80, 68.271, 65.02, 45.03, 33.65, 32.12, 31.23, 29.86, 29.84, 29.80, 29.78, 29.58, 29.54, 29.45, 29.41, 28.86, 27.09, 26.23, 25.99, 24.29, 24.22, 22.88, 14.30.

Example 25
Synthesis of N,N'-bis(2,6-diisopropylphenyl)-1-hexylpentathiophene-7-(iminohexyl-3,5-bis-dodecyloxybenzoate)perylene-3,4,9,10-tetra carboxydiimide (SP5TH)
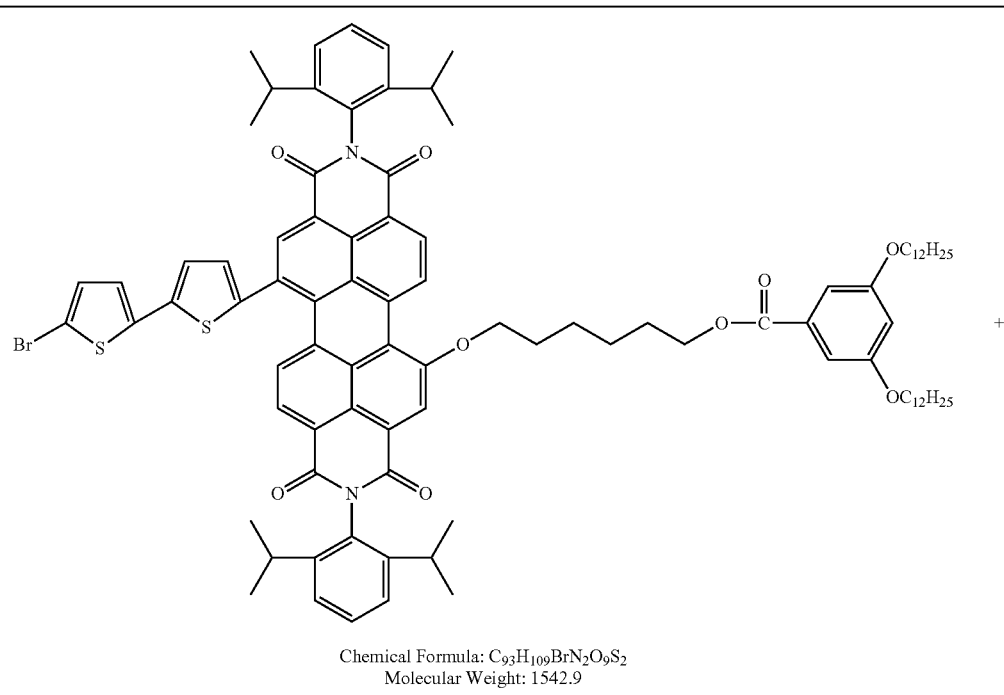
Chemical Formula: $C_{93}H_{109}BrN_2O_9S_2$
Molecular Weight: 1542.9
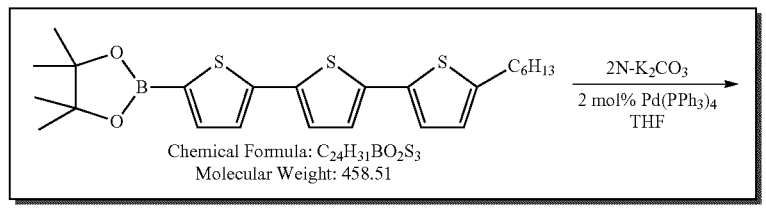
Chemical Formula: $C_{24}H_{31}BO_2S_3$
Molecular Weight: 458.51
2N-$K_2CO_3$
2 mol% Pd(PPh$_3$)$_4$
THF
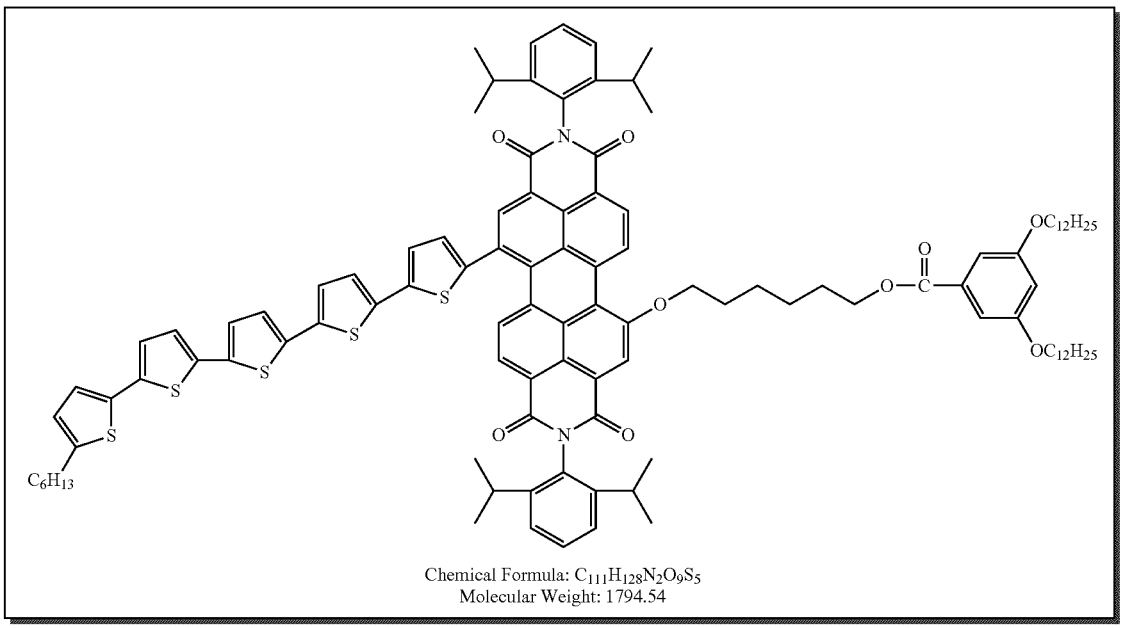
Chemical Formula: $C_{111}H_{128}N_2O_9S_5$
Molecular Weight: 1794.54

The perylene 2-bromobithiophene bisimide ester (0.308 g, 0.2 mmol) was dissolved in 25 mL dry THF and a solution of 2N $K_2CO_3$ (3 mL) was added into the reaction mixture. Then 2 mol % (0.005 g) tetrakis(triphenylphosphine) palladium(0) and hexylterthiophene borate (0.18 g, 0.4 g) were added. The resulting reaction mixture was refluxed for 24 h in $N_2$, before being poured into water and acidifying with 2N—HCl. The aqueous layer was extracted with MC and the organic extracts were dried over magnesium sulfate. The solvent was removed by rotary evaporation and the residue was purified by a column (silica gel, 20% EA and n-hexane) to yield 40% of the product as a green solid. $^1$H-NMR (300 MHz, $CDCl_3$) δ 8.92 (d, 1H), 8.76 (s, 1H), 8.66 (d, 1H), 8.36 (d, 1 H), 8.29 (s, 1H), 8.12 (d, 1H), 7.44-7.54 (m, 2H), 7.32-7.38 (m, 4H), 7.18 (dd, 1H), 7.12 (dd, 1H), 7.01-7.11 (m, 6H), 6.9 (t, 2H), 6.68 (d, 1H), 6.59 (t, 1H), 6.1-6.07 (br, NH), 4.28 (t, 2H), 3.86 (t, 4H), 3.52 (t, 2H), 2.66-2.82 (septet, 6H), 1.38-1.8 (m, 8H), −1.44 (m, 8H), 1.22-1.34 (m, 40H), 1.14-1.20 (m, 24H), 0.82 (t, 9H). $^{13}$C-NMR (300 MHz, $CDCl_3$) δ 166.74 (C=O), 163.81, 163.72, 163.65, 160.38, 156.46, 147.58, 145.90, 143.16, 139.67, 137.27, 137.09, 136.89, 136.53, 135.59, 135.05, 132.62, 132.27, 132.02, 131.36, 131.01, 130.87, 130.42, 130.33, 130.18, 129.80, 128.343, 128.13, 126.52, 125.00, 124.76, 124.67, 124.25, 124.2, 123.22, 122.69, 121.37, 120.29, 119.59, 115.61, 107.97, 106.44, 100.34, 86.73, 76.80, 68.271, 65.02, 45.03, 33.65, 32.12, 31.23, 29.86, 29.84, 29.80, 29.78, 29.58, 29.54, 29.45, 29.41, 28.86, 27.09, 26.23, 25.99, 24.29, 24.22, 22.88, 14.30.*

Example 26

Synthesis of N,N'-bis(2,6-diisopropylphenyl)-1-bromoterthiophene-7-(iminohexyl-3,5-bis-dodecyloxybenzoate)perylene-3,4,9,10-tetracarboxydiimide

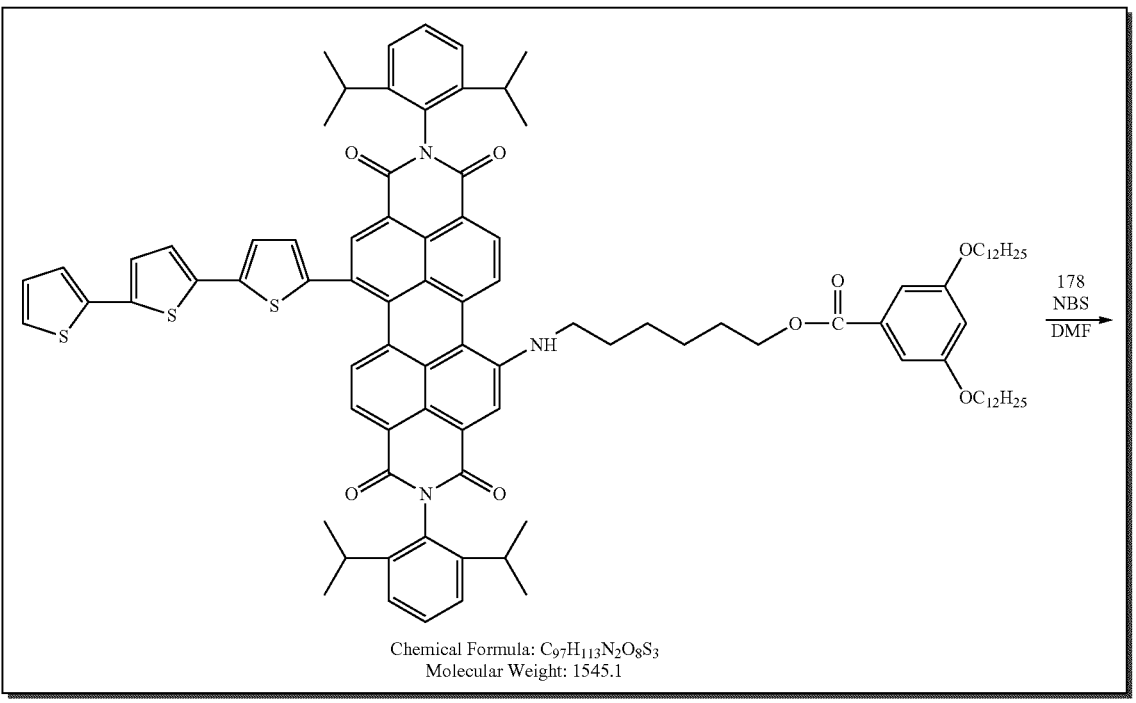

Chemical Formula: $C_{97}H_{113}N_2O_8S_3$
Molecular Weight: 1545.1

-continued

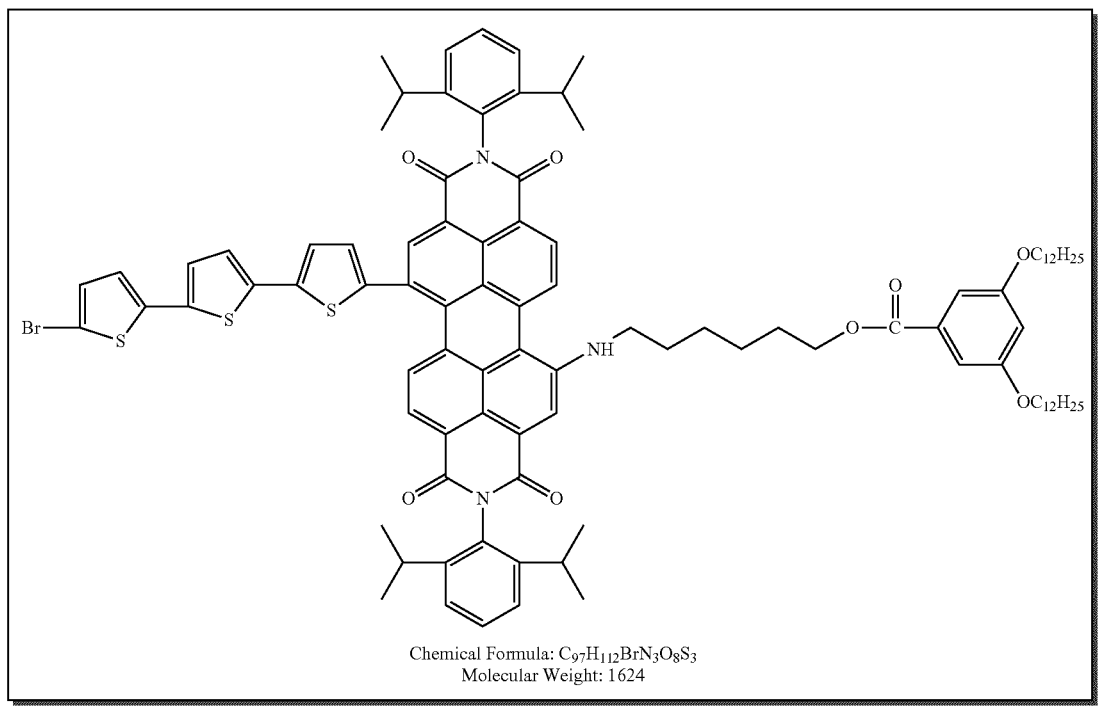

Chemical Formula: $C_{97}H_{112}BrN_3O_8S_3$
Molecular Weight: 1624

To a solution of perylene terthiophene bisimide ester (0.309 g, 0.2 mmol) in 10 mL of dry DMF under nitrogen in the dark, a solution of NBS (0.0356 g, 0.2 mmol) in DMF (3 mL) was added dropwise at 0° C. The resulting green solution was stirred at RT under $N_2$ overnight. The reaction mixture was poured into the crushed ice. The mixture was extracted with MC, washed with water and 2N—HCl solution and then organic extract was stored over $MgSO_4$. The solvent was removed by a rotary evaporator; the crude solid was purified by a column in 10% EA and hexane to obtain the tilled product (62%) as a green colored solid. $^1$H-NMR (300 MHz, $CDCl_3$) δ 8.92 (d, 1H), 8.76 (s, 1H), 8.68 (d, 1H), 8.34 (d, 1 H), 8.30 (s, 1H), 8.12 (d, 1H), 7.44-7.54 (m, 2H), 7.34-7.38 (m, 4H), 7.21 (d, 1H), 7.12-7.18 (m, bithiophene 1H and Ar 2H), 6.98 (d, 1H), 6.92 (d, 1H), 6.90, (m, 2H), 6.58 (t, 1H), 6.02 (br, NH), 4.28 (t, 2H), 3.88 (t, 4H), 3.52 (t, 2H), 2.66-2.82 (septet, 4H), 1.7-1.8 (m, 6H), 1.38-1.44 (m, 6H), 1.22-1.34 (m, 36H), 1.14 (d, 24H), 0.83 (t, 6H).

Example 27

Synthesis of N,N'-bis(2,6-diisopropylphenyl)-1-sexithiophene-7-(iminohexyl-3,5-bis-dodecyloxy-benzoate)perylene-3,4,9,10-tetra carboxydiimide (SP6T)

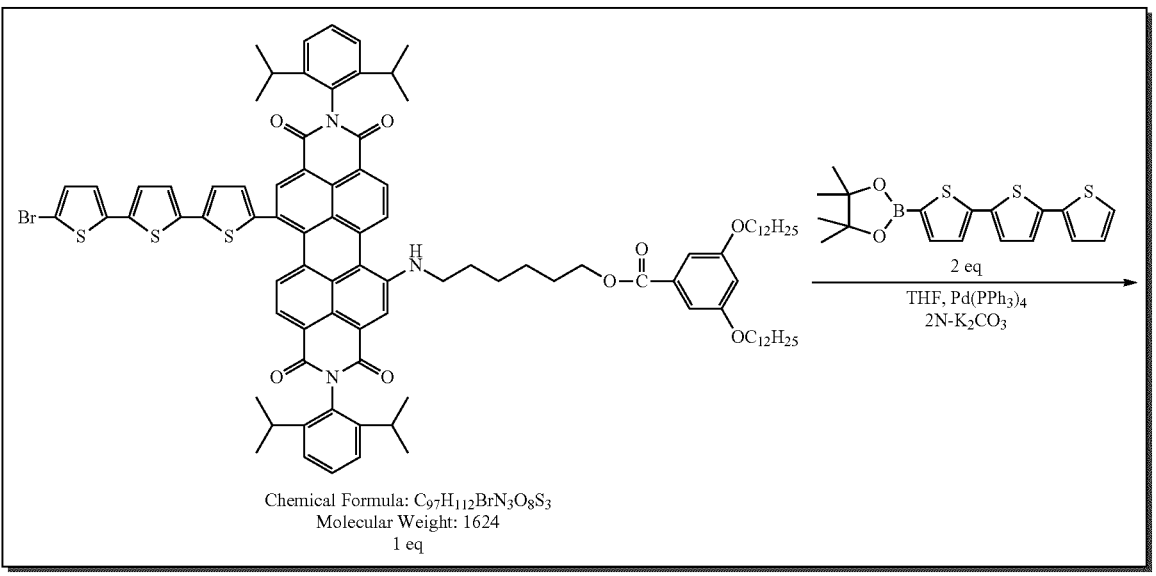

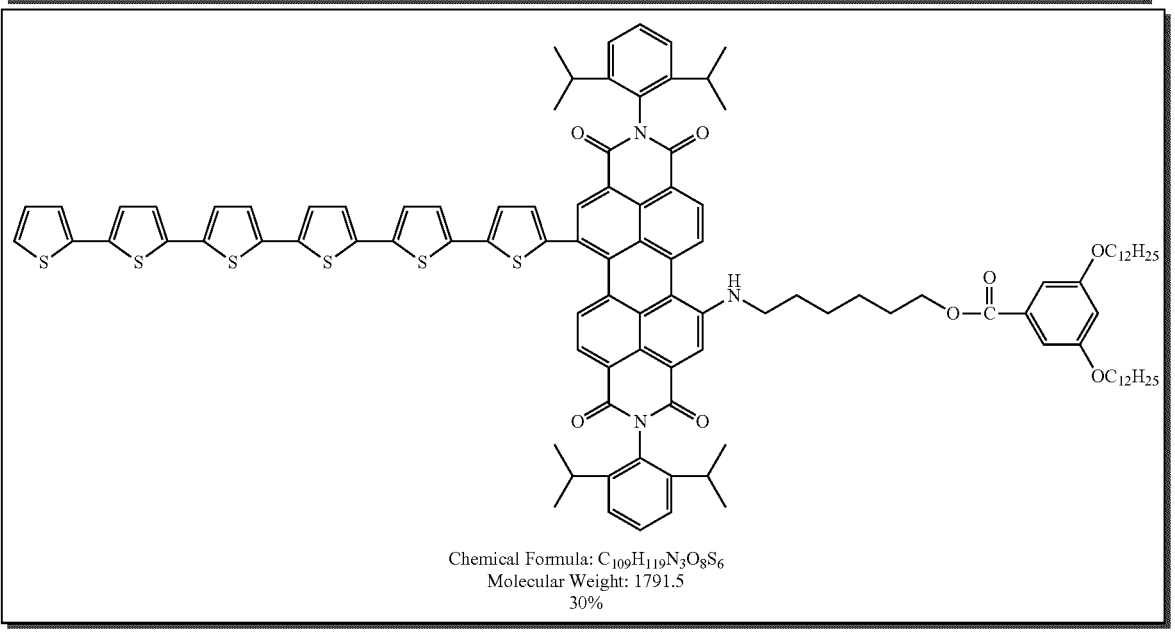

The perylene 2-bromoterthiophene bisimide ester (0.812 g, 0.5 mmol) was dissolved in 25 mL dry THF and a solution of 2N $K_2CO_3$ (6 mL) was added into the reaction mixture. Then 2 mol % (12 mg) tetrakis(triphenylphosphine) palladium(0) and terthiophene borate (0.38 g, 1 mmol) were added into the reaction mixture. The reaction mixture was refluxed for 24 h in $N_2$ before being poured into water, and acidifying with 2N—HCl. The aqueous layer was extracted with MC and the organic extracts were dried over magnesium sulfate. The solvent was removed by rotary evaporation and the residue was purified by a column (Silica gel, 20% EA and n-hexane) to yield 30% of the product as a green solid. $^1$H-NMR (300 MHz, $CDCl_3$) δ 8.92 (d, 1H), 8.76 (s, 1H), 8.66 (d, 1H), 8.36 (d, 1 H), 8.29 (s, 1H), 8.12 (d, 1H), 7.44-7.54 (m, 2H), 7.3-7.38 (m, 4H), 7.20 (dd, 3H), 7.16 (d, 1H), 7.12 (d, 2H), 7.01-7.11 (m, 9H), 6.59 (t, 1H), 6.1-6.07 (br, NH), 4.28 (t, 2H), 3.88 (t, 4H), 3.52 (t, 2H), 2.66-2.82 (septet, 4H), 1.7-1.8 (m, 8H), 1.38-1.44 (m, 8H), 1.22-1.34 (m, 32H), 1.14-1.20 (m, 24H), 0.82 (t, 6H). $^{13}$C-NMR (300 MHz, $CDCl_3$) δ 166.74 (C=O), 163.81, 163.72, 163.65, 160.38, 156.46, 147.58, 145.90, 143.16, 139.67, 137.27, 137.09, 136.89, 136.53, 135.59, 135.05, 132.62, 132.27, 132.02, 131.36, 131.01, 130.87, 130.42, 130.33, 130.18, 129.80, 128.343, 128.13, 126.52, 125.00, 124.76, 124.67, 124.25, 124.2, 123.22, 122.69, 121.37, 120.29, 119.59, 115.61, 107.97, 106.44, 100.34, 86.73, 76.80, 68.271, 65.02, 45.03, 33.65, 32.12, 31.23, 29.86, 29.84, 29.80, 29.78, 29.58, 29.54, 29.45, 29.41, 28.86, 27.09, 26.23, 25.99, 24.29, 24.22, 22.88, 14.30.

Example 28

Synthesis of N,N'-bis(2,6-diisopropylphenyl)-1-hexylsexithiophene-7-(iminohexyl-3,5-bis-dodecyloxybenzoate)perylene-3,4,9,10-tetra carboxydiimide (SP6TH)

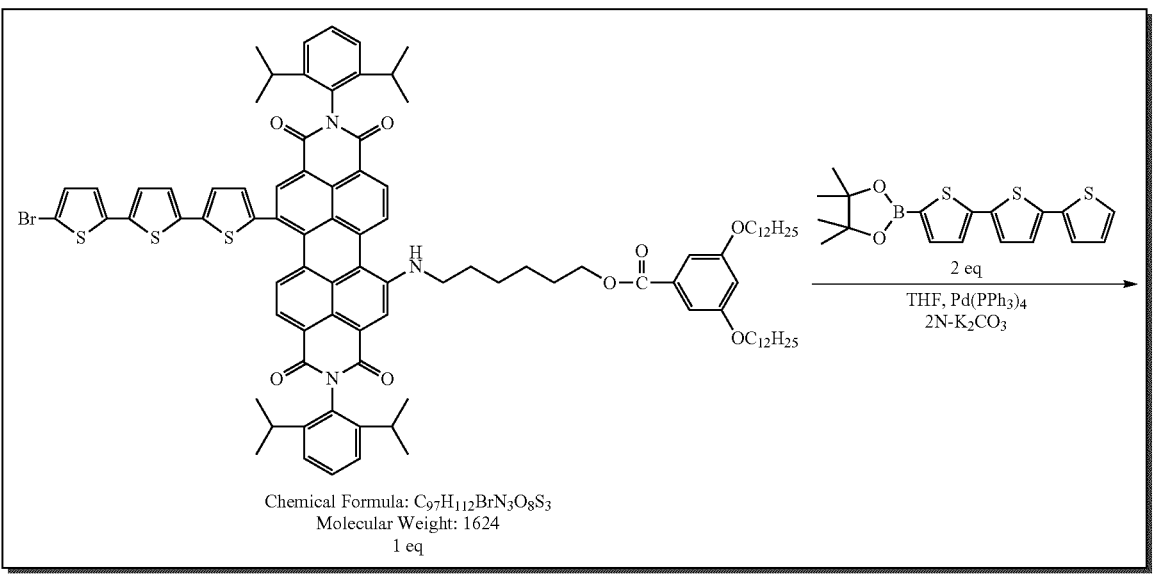

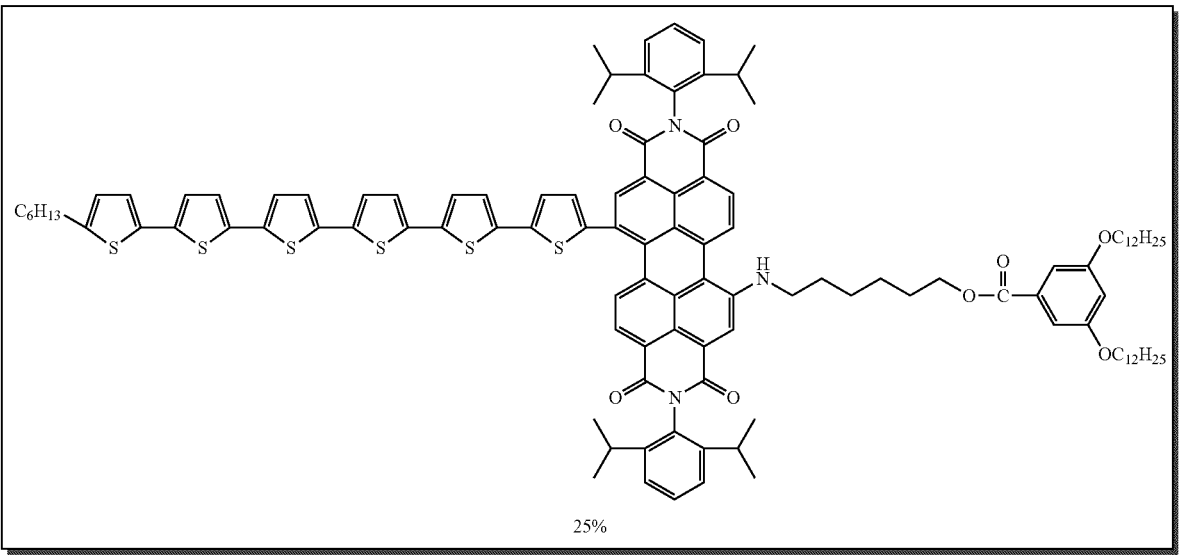

The perylene bormoterthiophene bisimide ester (0.812 g, 0.5 mmol) was dissolved in 25 mL dry THF and a solution of 2N $K_2CO_3$ (3 mL) was added into the reaction mixture. Then 2 mol % (12 mg) tetrakis(triphenylphosphine) palladium(0) and 2-hexylterthiophene borate (0.45 g, 1 mmol) were added into the reaction mixture. The reaction mixture was refluxed for 24 h in $N_2$ before being poured into water and acidifying with 2N—HCl. The aqueous layer was extracted with MC and the organic extracts were dried over magnesium sulfate. The solvent was removed by rotary evaporation and the residue was purified by a column (silica gel, 20% EA and n-hexane) to yield 25% of the product as a green solid. $^1$H-NMR (300 MHz, $CDCl_3$) δ 8.92 (d, 1H), 8.76 (s, 1H), 8.66 (d, 1H), 8.36 (d, 1 H), 8.29 (s, 1H), 8.12 (d, 1H), 7.44-7.54 (m, 2H), 7.32-7.38 (m, 4H), 7.18 (dd, 2H), 7.12 0 (d, 2H), 7.01-7.11 (m, 6H), 6.9 (t, 2H), 6.68 (d, 1H), 6.59 (t, 1H), 6.01-6.07 (br, NH), 4.28 (t, 2H), 3.86 (t, 4H), 3.52 (t, 2H), 2.66-2.82 (septet, 6H), 1.38-1.8 (m, 8H), −1.44 (m, 8H), 1.22-1.34 (m, 40H), 1.14-1.20 (m, 24H), 0.82 (t, 9H). $^{13}$C-NMR (300 MHz, $CDCl_3$) δ166.74 (C=O), 163.81, 163.72, 163.65, 160.38, 156.46, 147.58, 145.90, 143.16, 139.67, 137.27, 137.09, 136.89, 136.53, 135.59, 135.05, 132.62, 132.27, 132.02, 131.36, 131.01, 130.87, 130.42, 130.33, 130.18, 129.80, 128.343, 128.13, 126.52, 125.00, 124.76, 124.67, 124.25, 124.2, 123.22, 122.69, 121.37, 120.29, 119.59, 115.61, 107.97, 106.44, 100.34, 86.73, 76.80, 68.271, 65.02, 45.03, 33.65, 32.12, 31.23, 29.86, 29.84, 29.80, 29.78, 29.58, 29.54, 29.45, 29.41, 28.86, 27.09, 26.23, 25.99, 24.29, 24.22, 22.88, 14.30.

Example 29

Determination of HOMO and LUMO Levels

Electrochemical measurements were performed by using a CHI600C (CH Instruments Inc., USA) with an electrochemical cell consisting of a platinum electrode (2 mm diameter), a Pt wire counter electrode, and a Ag/AgCl reference electrode at RT. 0.1 M Tetrabutylammonium perchlorate ($Bu_4NClO_4$, TBAP) in dichloromethane (Aldrich, HPLC grade) was used as a supporting electrolyte (scan rate 50 $mVs^{-1}$).

FIGS. 1a-e show cyclic voltammograms of the TCPTCDIs of the present invention. The HOMO levels of SP2TH~SP6TH were determined as −5.35 eV, −5.30 eV, −5.28 eV, −5.14 eV, and −5.13 eV, respectively. An increase in thiophene conjugation resulted in a slight increase in HOMO levels (0.22 eV).

Figure 3:
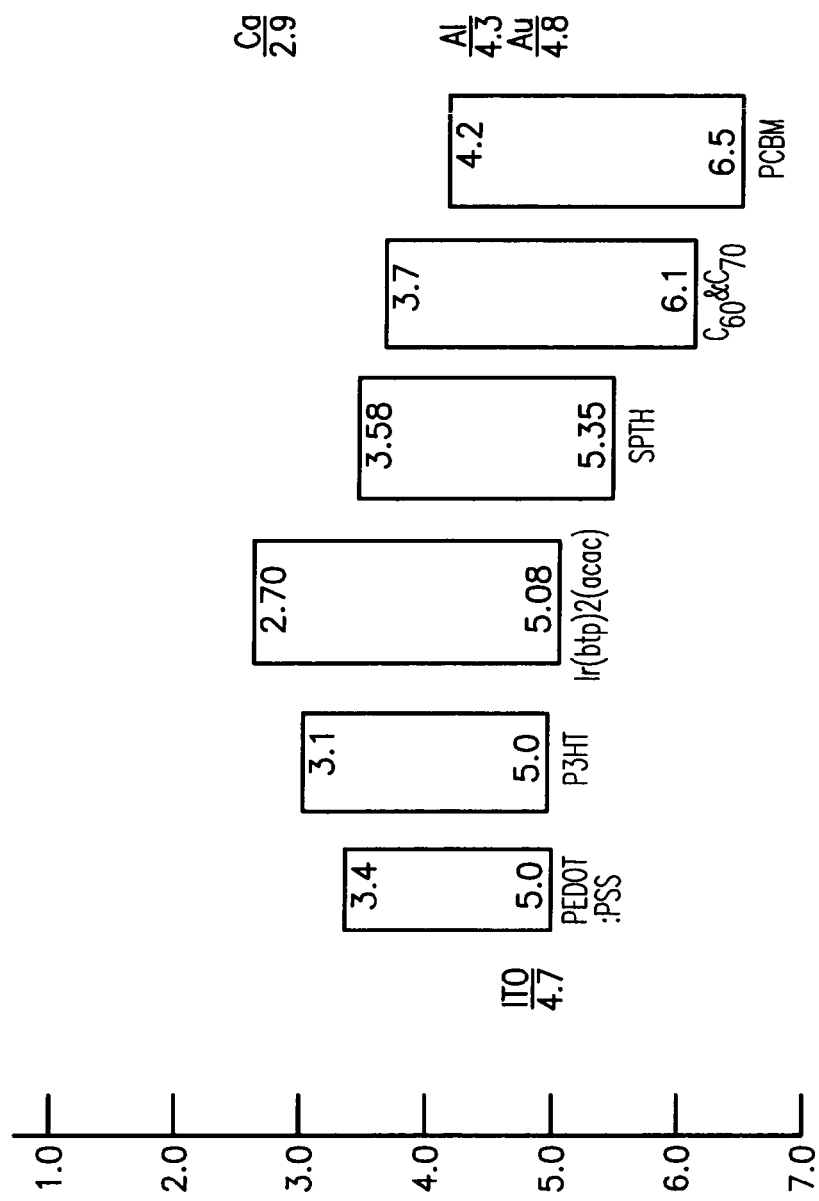

FIGS. 2 and 3 show energy band diagrams of the TCPTCDIs synthesized in the above examples and other OPV materials. Depending on the energy levels of OPV materials, TCPTCDIs could be an electron donor toward C60, C70 and PCBM or an acceptor toward P3HT and iridium complex.

Figure 4:
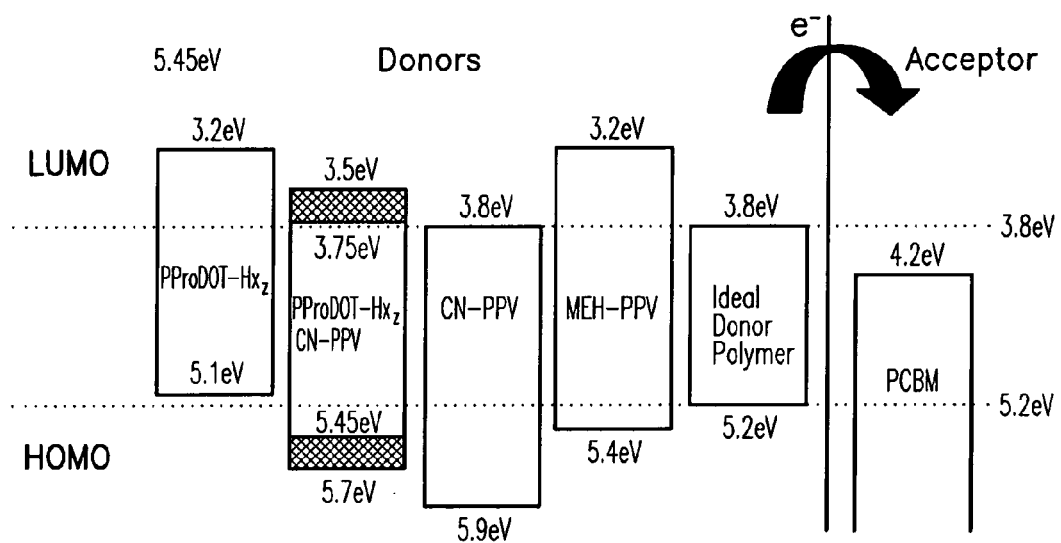
FIG. 4 is a band diagram of an ideal electron donor for fullerene derivative [6,6]-phenyl-$C_{61}$-butyric acid methyl ester (PCBM).

Considering their HOMO and LUMO levels, the TCPTCDIs of the present invention could be used as an ideal electron donor for a PCBM acceptor. Reynolds et al. reported that the energy levels of an ideal electron donor for the PCBM acceptor should be −3.8 eV~−5.2 eV (see, Reynolds et al, *Macromolecules*, 38:5359 (2005), Leclerc et al, *J. Am. Chem. Soc.* 130:732 (2008), and Scharber et al, *J. Adv. Mater.* 18: 789 (2006)). As shown in FIG. 4, the oligothiophene-conjugated perylene tetracarboximide has a LUMO of −3.58 eV and a HOMO of −5.35 eV, which are almost identical to the values ideal for being a donor material for PCBM.

Example 30

UV-Vis Absorption Spectra

Figure 5A:
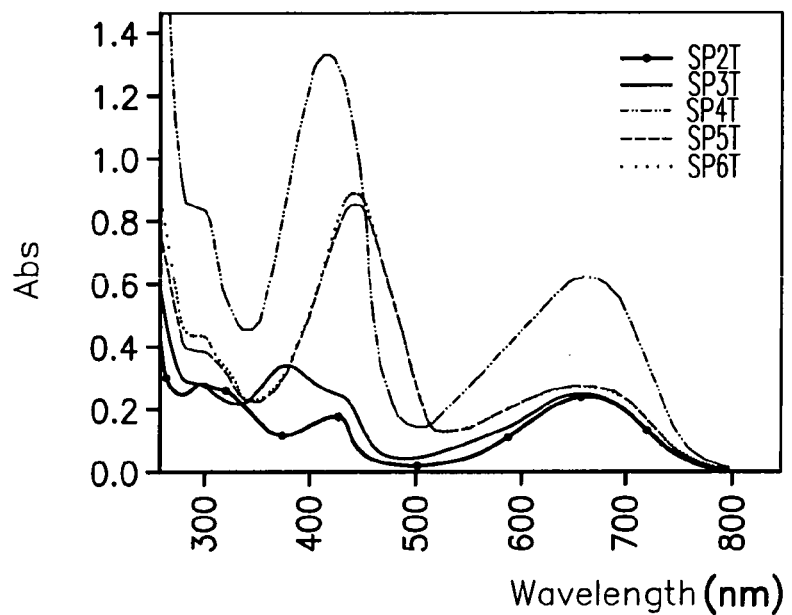
FIGS. 5a-b are UV-vis absorption spectra of the TCPTC-DIs of the present invention.
Figure 5B:
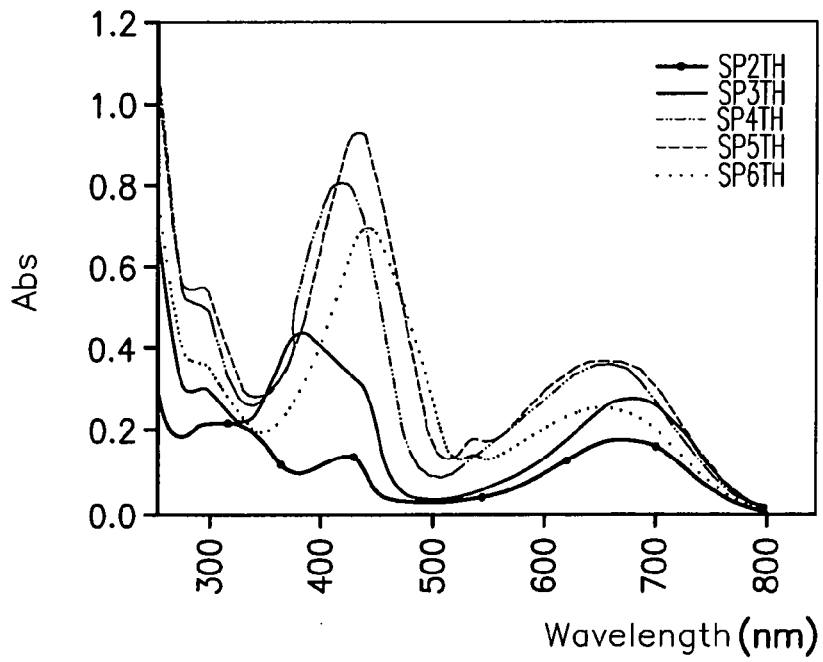

The UV-vis absorption spectra of the compounds obtained in Examples 1-5 above were measured by using a Jasco V-570 UV-vis spectrometer ($5 \times 10^{-5}$ M in chloroform). The results are shown in FIGS. 5a-b and Tables 1 and 2 below.

TABLE 1

UV-vis absorption spectra of SP2T to SP6T

| Compounds | $\lambda_{max}$ of blue region | $\lambda_{max}$ of red region | Band gap $E_g$ | Molar absorptivity ($\epsilon$) | |
|---|---|---|---|---|---|
| SP2T | 426 nm | 666 nm | 1.55 (775 nm) | $2.5 \times 10^4$ | |
| SP3T | 375 nm | 665 nm | 1.55 (775 nm) | $2.6 \times 10^4$ | |
| SP4T | 411 nm | 664 nm | 1.55 (775 nm) | $6.4 \times 10^4$ | Strongest |
| SP5T | 439 nm | 662 nm | 1.55 (775 nm) | $2.8 \times 10^4$ | |
| SP6T | 439 nm | 665 nm | 1.55 (775 nm) | $2.8 \times 10^4$ | |

TABLE 2

UV-vis absorption spectra of SP2TH to SP6TH

| Compounds | $\lambda_{max}$ of blue region | $\lambda_{max}$ of red region | $E_{op}$ | $E_{HOMO}$ (eV) | $E_{LUMO}$ (eV) | Molar absorptivity ($\epsilon$) |
|---|---|---|---|---|---|---|
| SP2TH | 424 nm | 672 nm | 1.55 | 5.35 | 3.80 | $1.8 \times 10^4$ |
| SP3TH | 381 nm | 678 nm | 1.55 | 5.30 | 3.75 | $2.7 \times 10^4$ |
| SP4TH | 424 nm | 660 nm | 1.55 | 5.28 | 3.73 | $3.7 \times 10^4$ |
| SP5TH | 430 nm | 647 nm | 1.55 | 5.14 | 3.59 | $3.7 \times 10^4$ |
| SP6TH | 440 nm | 650 nm | 1.55 | 5.13 | 3.58 | $2.5 \times 10^4$ |

As shown in the above results, the SPT derivatives have similar or identical absorption behaviour as those of the SPTH derivatives, and the quarterthiophene-conjugated PTCDI has the strongest molar absorptivity. All oligothiophene-conjugated PTCDIs exhibit strong absorption bands up to the end of the visible region around 800 nm. Thus, they can be used as low band gap OPV materials.

Example 31

Thermogravimetric Analysis

Figure 6:
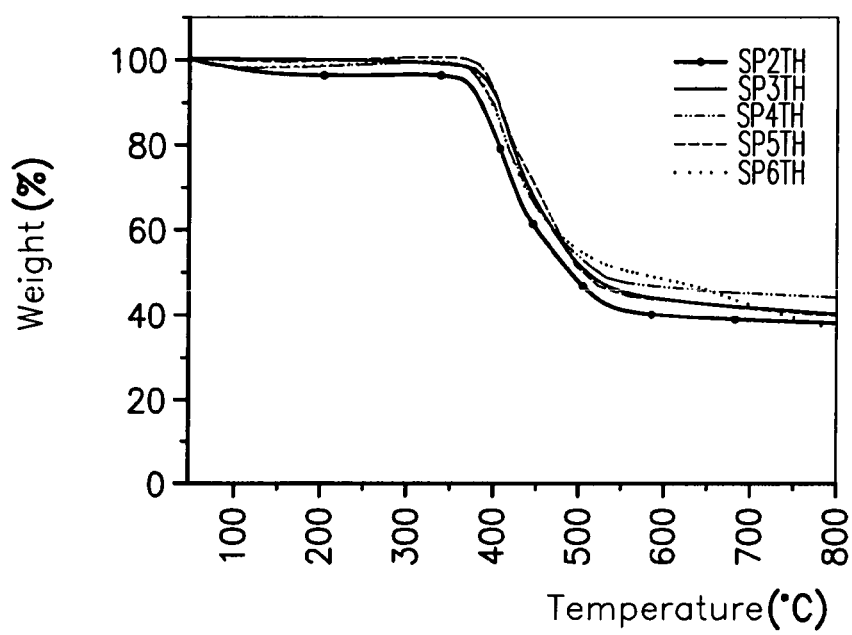
FIG. 6 shows the thermogravimetric analysis (TGA) curves of the TCPTCDIs of the present invention.

Thermal gravimetric analysis (TGA) was carried out on a Mettler Toledo TGA/SDTA 851 (Mettler-Toledo GmbH, Schwerzenbach, Switzerland), and differential scanning calorimetric analysis (DSC) was performed on a Perkin-Elmer Pyris 1 instrument (U.S.A) under $N_2$ atmosphere at a rate of 10° C./min. As the temperature increased, the temperature, when 5% by weight of the test compound decreases, was measured. FIG. 6 shows the TGA curves of the TCPTCDI derivatives. The TGA thermograms of the oligo-TCPTCDI derivatives showed that 5% weight losses ranged from 362 to 388° C. and that oligo-TCPTCDIs were stable at least up to 360° C., indicating that TCPTCDI derivatives are thermally stable enough for OPV device applications.

Example 32

Comparison of Absorption Behaviors

Figure 7:
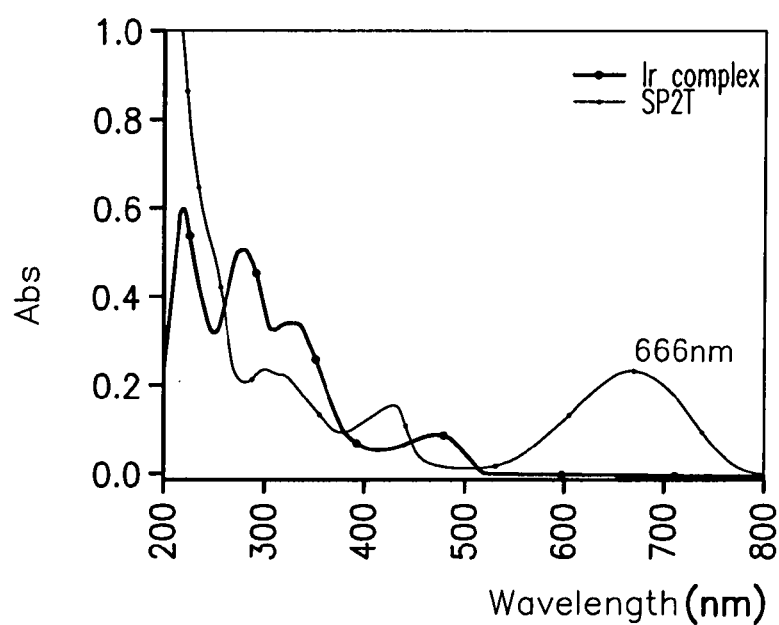
FIG. 7 compares the UV-vis absorption spectra of the TCPTCDI of the present invention and the iridium complex.

The UV-vis absorption behavior of TCPTCDI was compared with that of an Ir complex ($Ir(btp)_2(acac)$) which is a conventional donor material in OPV devices. The absorption spectrum of the Ir complex was measured by using the same method of Example 30. FIG. 7 shows data comparing the UV-vis absorption behaviors of TCPTCDI and the Ir complex, where TCPTCDI (SP2T) covers a much longer (red) wavelength region than the iridium complex. The molar absorptivity at the longest $\lambda_{max}$ of SP2T ($2.4 \times 10^4$) was 4 times larger than that of the iridium complex at 475 nm ($6.0 \times 10^3$). Due to the longer absorption wavelength covered and the higher absorptivity at the longest $\lambda_{max}$, TCPTCDIs are capable as more efficient donor molecules than the Ir complex.

Example 33

Determination of Quenching Rate

TCPTCDIs may also be used as acceptor molecules when a donor molecule having a higher energy band than TCPTCDI is employed. For example, Ir(btp)$_2$(acac) or P3HT can be used as a donor molecule (see FIG. 4). In this example, the quenching of triplet phosphorescence of the iridium complex Ir(btp)$_2$(acac) was determined by using TCPTCDIs.

Figure 8:
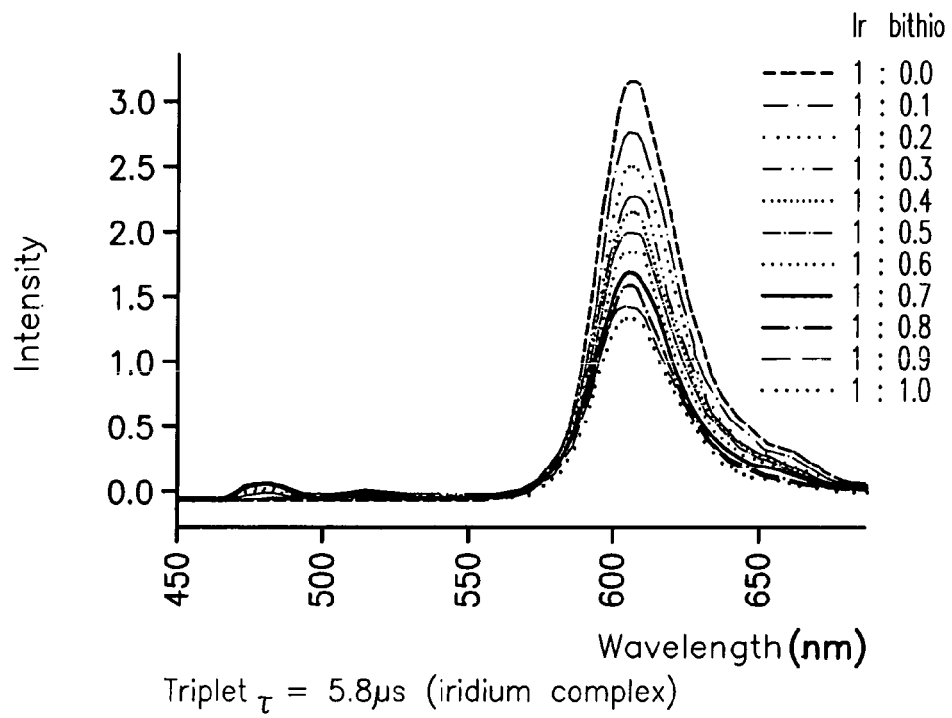
FIG. 8 shows the phosphorescent quenching spectra of an iridium complex by the TCPTCDIs of the present invention.
Figure 9:
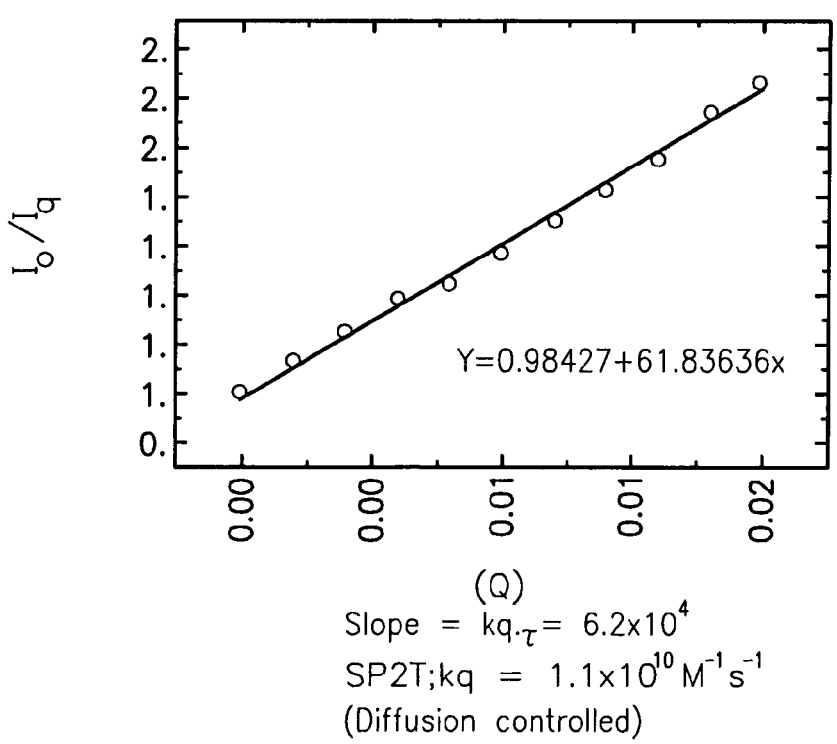
FIG. 9 is a Stern-Volmer plot of the quenching of an iridium complex by the TCPTCDIs of the present invention.

The phosphorescent quenching spectra of the Ir complex measured by varying the ratio of the Ir complex to SP2T is shown in FIG. 8. FIG. 9 is a Stern-Volmer plot of the quenching of the iridium complex by the TCPTCDIs. The quenching rate constant was calculated from the triplet lifetime (iridium complex) and the slope of the Stern-Volmer plot. The quenching rate constant using SP2T was calculated as $1.1 \times 10^{10}$ $M^{-1}s^{-1}$. Other quenching rate constants using TCPTCDIs are given in Table 3 below.

TABLE 3

Quenching rate constants

| Compounds | Rate Constants ($M^{-1}s^{-1}$) |
| --- | --- |
| SP2T | $1.1 \times 10^{10}$ |
| SP3T | $3.1 \times 10^{10}$ |
| SP4T | $2.7 \times 10^{10}$ |
| SP5T | $2.5 \times 10^{10}$ |
| SP6T | $2.7 \times 10^{10}$ |

All SPTs which contain bi- to sexi-thiophene moieties exhibit extremely high phosphorescent quenching rate constants, i.e., $1.1 \sim 3.1 \times 10^{10}$ (diffusion-controlled). It is conceived that the high quenching rate constants are the result of a real electron transfer from the excited iridium to the TCPTCDIs.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

The invention claimed is:

1. A compound of Formula I:

Formula (I)

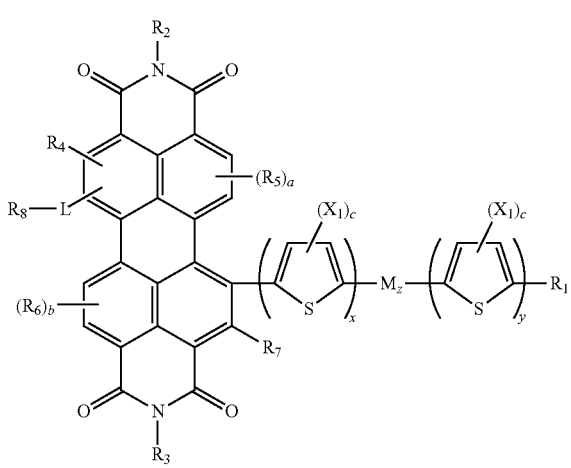

wherein:

M is represented by the following formula:

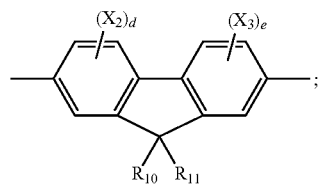

$R_1, R_2, R_3, R_4, R_5, R_6, R_7, R_8, R_{10}, R_{11}, X_1, X_2$, and $X_3$ are the same or different at each occurrence and are selected from the group consisting of —H, —F, —Cl, —Br, —NO$_2$, —CN, a straight or branched $C_{1-20}$ alkyl, a $C_{2-20}$ alkene, a $C_{2-20}$ alkyne, a $C_{3-20}$ cyclic alkyl, a straight or branched $C_{1-20}$ alkoxy, a $C_{1-20}$ dialkylamino, a $C_{4-20}$ polyoxaalkyl, a $C_{4-20}$ polythioalkyl, a $C_{4-20}$ polyazaalkyl, a $C_{4-14}$ aryl, and a $C_{4-14}$ heteroaryl which may be substituted with one or more non-aromatic radicals;

L is selected from the group consisting of —NR$_9$—, —PR$_9$—, —O—, and —S—, wherein R$_9$ is selected from the group consisting of —H, —F, —Cl, —Br, —NO$_2$, —CN, a straight or branched $C_{1-20}$ alkyl, a $C_{2-20}$ alkene, a $C_{2-20}$ alkyne, a $C_{3-20}$ cyclic alkyl, a straight or branched $C_{1-20}$ alkoxy, a $C_{1-20}$ dialkylamino, a $C_{4-20}$ polyoxaalkyl, a $C_{4-20}$ polythioalkyl, a $C_{4-20}$ polyazaalkyl, a $C_{4-14}$ aryl, and a $C_{4-14}$ heteroaryl which may be substituted with one or more non-aromatic radicals;

a, b, and c are the same or different at each occurrence and are an integer from 0 to 2;

d and e are the same or different at each occurrence and are an integer from 0 to 3;

x is an integer from 1 to 4 and y is an integer from 0 to 4; and z is 0 or 1.

2. The compound according to claim 1, wherein R$_1$ is —H, a straight or branched $C_{1-20}$ alkyl, a $C_{4-20}$ polyoxaalkyl, a $C_{4-20}$ polythioalkyl, or a $C_{4-20}$ polyazaalkyl, which may be substituted with one or more non-aromatic radicals.

3. The compound according to claim 1, wherein R$_2$ and R$_3$ are $C_{4-14}$ aryl which may be substituted with one or more non-aromatic radicals.

4. The compound according to claim 3, wherein R$_2$ and R$_3$ are diisopropyl phenyl.

5. The compound according to claim 1, wherein R$_4$, R$_5$, R$_6$, and R$_7$ are —H.

6. The compound according to claim 1, wherein R$_8$ is a straight or branched $C_{1-20}$ alkyl which may be substituted with one or more substituents represented by the following formula:

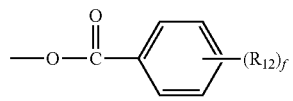

wherein R$_{12}$ is selected from the group consisting of —F, —Cl, —Br, —NO$_2$, —CN, a straight or branched $C_{1-20}$ alkyl, a $C_{2-20}$ alkene, a $C_{2-20}$ alkyne, a $C_{3-20}$ cyclic alkyl, a straight or branched $C_{1-20}$ alkoxy, a $C_{1-20}$ dialkylamino, a $C_{4-20}$ polyoxaalkyl, a $C_{4-20}$ polythioalkyl, a $C_{4-20}$ polyazaalkyl, a $C_{4-14}$ aryl, and a $C_{4-14}$ heteroaryl which may be substituted with one or more non-aromatic radicals, wherein, when f is an integer of at least 2, a plurality of $R_{12}$, may in turn together form a mono- or polycyclic ring, optionally aromatic; and f is an integer from 0 to 5.

7. The compound according to claim 6, wherein $R_8$-L- is represented by the following formula:

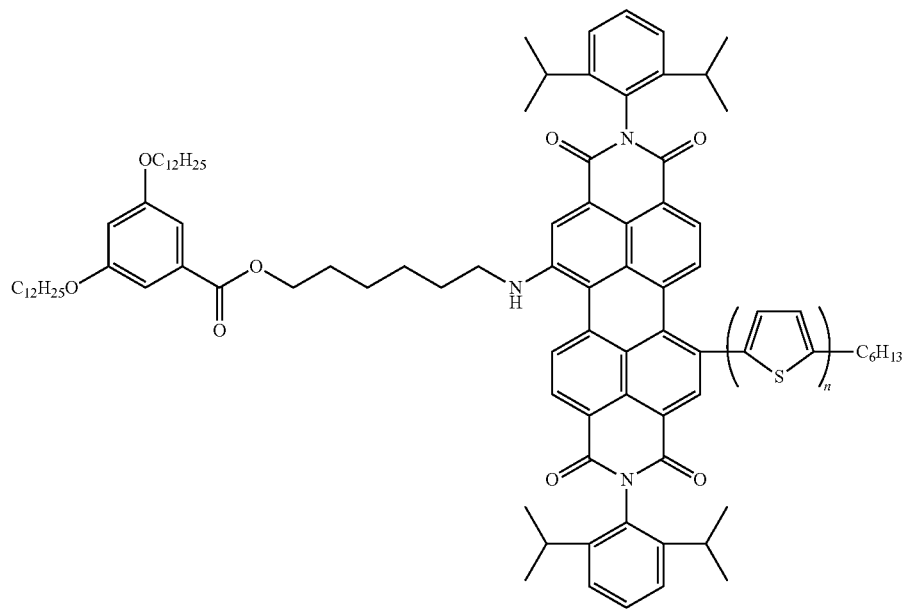

8. The compound according to claim 7, wherein the compound has the following formula:

Formula (II)

wherein n is an integer from 2 to 6.

9. The compound according to claim 1, wherein $R_1$ is a straight or branched $C_{1-20}$ alkyl, a $C_{2-20}$ alkene, a $C_{2-20}$ alkyne, a $C_{4-20}$ polyoxaalkyl, a $C_{4-20}$ polythioalkyl, or a $C_{4-20}$ polyazaalkyl, substituted with one or more cyano groups and/or carboxyl groups.

10. The compound according to claim 9, wherein the compound has the following formula:

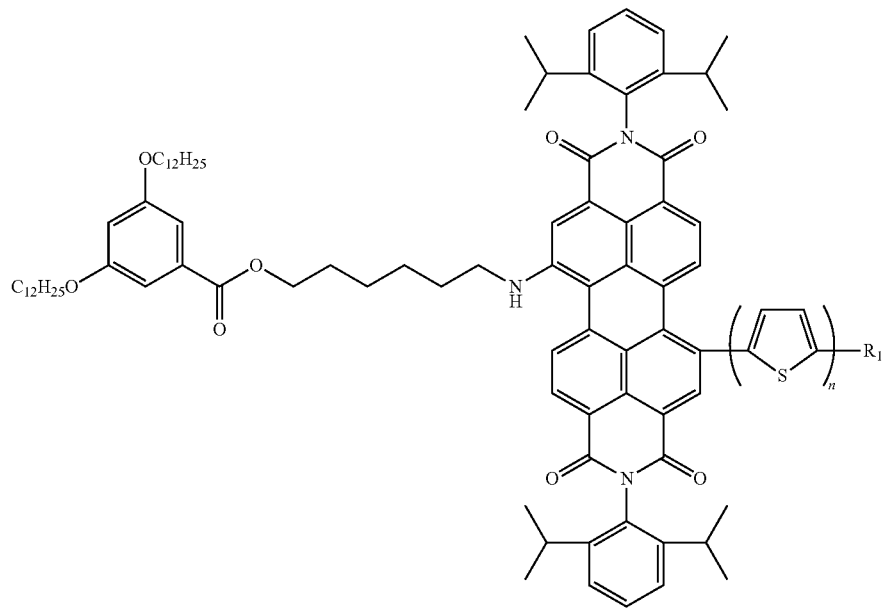
Formula (III)
wherein
R₁ is selected from the group consisting of
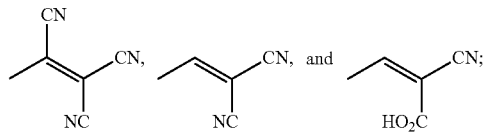
and
n is an integer from 2 to 6.
11. A molecular heterojunction material comprising the compound according to claim 1.
12. A photovoltaic device comprising the molecular heterojunction material according to claim 11.
* * * * *